(12) United States Patent
Kuzelka et al.

(10) Patent No.: US 11,511,070 B2
(45) Date of Patent: Nov. 29, 2022

(54) SYSTEMS AND METHOD FOR AN INDUCTIVE ANESTHETIC AGENT LEVEL SENSOR

(71) Applicant: GE Precision Healthcare LLC, Milwaukee, WI (US)

(72) Inventors: Russell James Kuzelka, McFarland, WI (US); Joseph James Lacey, Cambridge, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 728 days.

(21) Appl. No.: 16/569,583

(22) Filed: Sep. 12, 2019

(65) Prior Publication Data
US 2021/0077769 A1    Mar. 18, 2021

(51) Int. Cl.
| | |
|---|---|
| *A61M 16/18* | (2006.01) |
| *G01F 23/26* | (2022.01) |
| *G01F 23/72* | (2006.01) |
| *G01D 5/20* | (2006.01) |

(52) U.S. Cl.
CPC .......... *A61M 16/183* (2013.01); *G01F 23/26* (2013.01); *A61M 2230/437* (2013.01); *G01D 5/2046* (2013.01); *G01F 23/72* (2013.01)

(58) Field of Classification Search
CPC ............ G01F 23/26–268; G01F 23/72; G01D 5/2046; A61M 2230/437
See application file for complete search history.

(56) References Cited

U.S. PATENT DOCUMENTS

| | | | |
|---|---|---|---|
| 4,165,641 A | | 8/1979 | Pomerantz et al. |
| 5,005,407 A | * | 4/1991 | Koon ............... G01F 23/266 73/304 C |
| 5,103,893 A | * | 4/1992 | Naganuma ........... G01F 23/26 164/451 |
| 6,192,753 B1 | * | 2/2001 | Czarnek ............ G01D 5/2046 73/290 R |
| 2013/0255676 A1 | * | 10/2013 | Kuehl ................ G01F 23/266 128/203.12 |

* cited by examiner

*Primary Examiner* — Valerie L Woodward

(57) ABSTRACT

Systems and methods are provided for anesthetic agent level sensing. In one embodiment, a system for an inductive level sensor for an anesthetic vaporizer includes a measurement target positioned around a rod that extends within a chamber configured to hold liquid anesthetic agent, the rod configured to be at least partially submerged in the liquid anesthetic agent and the measurement target configured to slide vertically along a length of the rod and rest on a surface of the liquid anesthetic agent, and a strip of inductive transmitter coils and receiver coils positioned external to the chamber, a length of the strip aligned with the length of the rod, the transmitter coils configured to generate a magnetic field that surrounds the rod and the measurement target and the receiver coils configured to sense changes in the generated magnetic field at a vertical location of the measurement target on the rod.

20 Claims, 8 Drawing Sheets

SYSTEMS AND METHOD FOR AN INDUCTIVE ANESTHETIC AGENT LEVEL SENSOR

FIELD

Embodiments of the subject matter disclosed herein relate to anesthesia systems, and more particularly, to systems and methods for monitoring a level of anesthetic agent remaining in an anesthetic vaporizer.

BACKGROUND

During some medical procedures, such as surgical procedures, a patient may be placed under general anesthesia by administrating an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form at a vaporizing chamber. A carrier gas (e.g., a mixture of oxygen and fresh air) may flow into the vaporizing chamber and blend (e.g., mix and converge) with the anesthetic agent vapors generated by the vaporizing chamber before flowing to the patient, where they may be introduced via inhalation, for example.

Conventional anesthetic vaporizers include a sump for storing the liquid anesthetic agent before it is metered to the vaporizing chamber via a pump. The sump may be controlled based on a level of the liquid anesthetic agent in the vaporizing chamber to ensure sufficient anesthetic agent is available for vaporization. Further, an operator (e.g., an anesthesiologist or other clinician) may monitor a level of liquid anesthetic agent in the sump, both before use and during use, to ensure sufficient anesthetic agent is available for delivery to the patient during the medical procedure.

BRIEF DESCRIPTION

In one embodiment, a system for an inductive level sensor for an anesthetic vaporizer includes a measurement target positioned around a rod that extends within a chamber configured to hold liquid anesthetic agent, the rod configured to be at least partially submerged in the liquid anesthetic agent and the measurement target configured to slide vertically along a length of the rod and rest on a surface of the liquid anesthetic agent, and a strip of inductive transmitter coils and receiver coils positioned external to the chamber, a length of the strip aligned with the length of the rod, the transmitter coils configured to generate a magnetic field that surrounds the rod and the measurement target and the receiver coils configured to sense changes in the generated magnetic field at a vertical location of the measurement target on the rod. In this way, the inductive level sensor may provide anesthetic agent level measurements with increased accuracy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
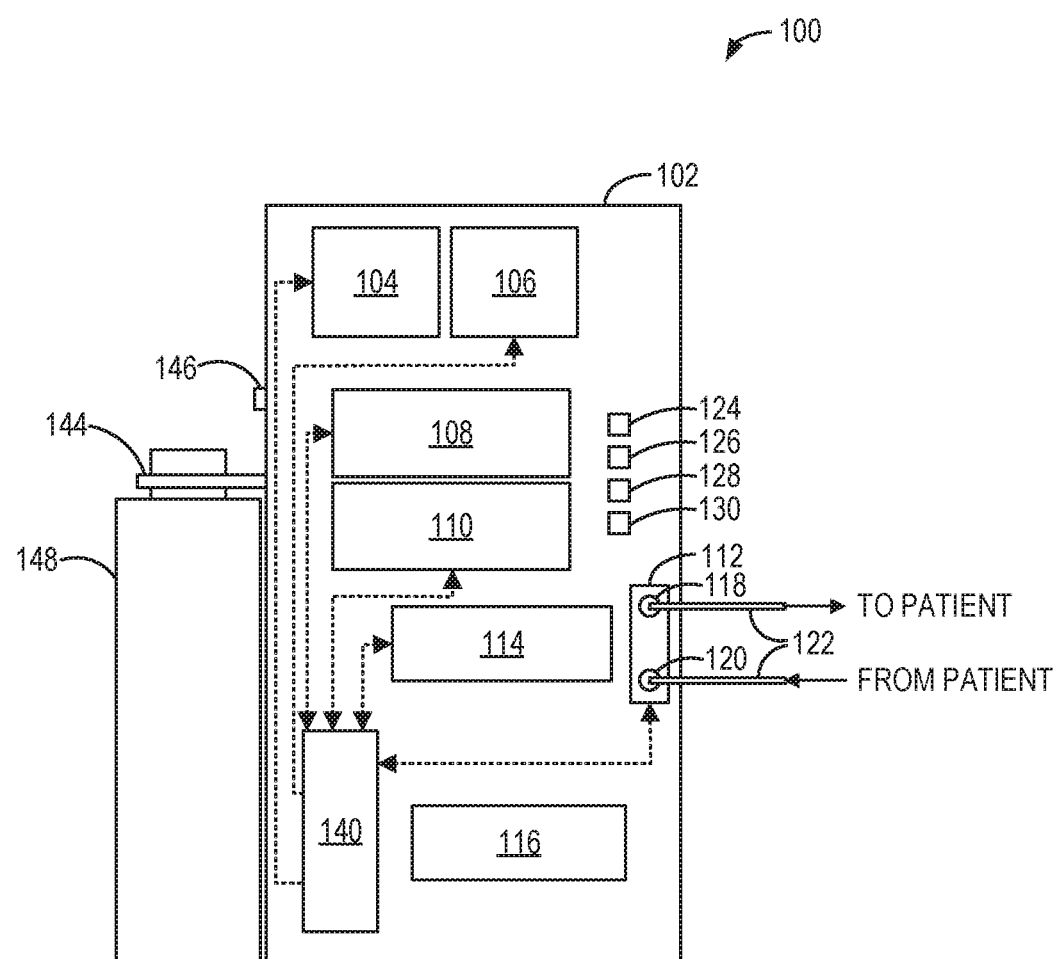
FIG. 1 schematically shows an exemplary embodiment of an anesthesia machine.

The following description relates to various embodiments for measuring and monitoring a level of liquid anesthetic agent in an anesthetic vaporizer, which may be included in an anesthesia machine. Currently available anesthetic agent level sensors, such as capacitive, acoustic/ultrasonic, and differential hydrostatic level sensors, may be affected by characteristics of the liquid anesthetic agent. For example, liquid anesthetic agents are halogenated solvents that may aggressively react with certain materials and/or deposit residues, such as a film composed of butylated hydroxytoluene (BHT), over time. As one example, changes to dielectric properties of the liquid anesthetic agent caused by BHT deposition over time may affect measurements made by capacitive level sensors. As another example, acoustic/ultrasonic level sensors may be impacted by changes in humidity and a temperature of the liquid anesthetic agent. As still another example, differential hydrostatic level sensors may be incompatible with the reactive anesthetic agents. As a result, the above-mentioned sensors may be unable to accurately measure anesthetic agent level, and therefore volume, across time and conditions.

Thus, according to embodiments disclosed herein, an inductive level sensor is provided that is not affected by changes in in the characteristics of the liquid anesthetic agent. In the embodiments disclosed herein, the inductive level sensor includes a measurement target positioned within a liquid-holding chamber of the anesthetic vaporizer and a printed circuit board positioned external to the liquid-holding chamber. According to embodiments disclosed herein, the measurement target is a metallic-plated float that vertically moves along a rod and sits at a surface of the liquid anesthetic agent. In the embodiments disclosed herein, the printed circuit board includes a strip of inductive coils, including both transmitter coils and receiver coils, along a length of the printed circuit board at a positon that overlaps with a length of the rod and the measurement target thereon. The transmitter coils are configured to generate a magnetic field that substantially surrounds the rod and the measurement target within the chamber, and the receiver coils are configured to sense changes in the generated magnetic field at a vertical location of the measurement target. Further, the printed circuit board may be coupled to an electronic controller, which may receive a signal output from the receiver coils corresponding to the vertical location of the measurement target, and the controller may use the signal output to determine a level and/or volume of liquid anesthetic agent in the chamber.

According to the embodiments disclosed herein, the chamber may be a vaporizing chamber configured to receive liquid anesthetic agent from a sump via a pump. In such embodiments, the rod may be comprised of a portion of a heat pipe configured to provide heat to the liquid anesthetic agent in the vaporizing chamber, and the measurement target may additionally include a sealing disc positioned on a top surface of the metallic-plated float. The sealing disc may be configured to block an opening to an output manifold during an overfilling condition. According to the embodiments disclosed herein, the chamber may be the sump. According to some such embodiments, the inductive level sensor may be a combined sensor that includes a first inductive coil strip and a first measurement target for measuring the level of liquid anesthetic agent in the vaporizing chamber and a second inductive coil strip and a second measurement target for measuring the level of liquid anesthetic agent in the sump. The first inductive coil strip and the second inductive coil strip may be printed on a shared circuit board and may output separate signals to the controller.

The embodiments disclosed herein may provide several advantages. For example, the inductive level sensor may measure a physical height of the measurement target, which is not sensitive to physical characteristics of the liquid anesthetic agent, increasing an accuracy of the measurements made by the level sensor. Further, the physical height reproducibly relates to a calculable volume of the liquid anesthetic agent, enabling higher accuracy volume calculation. As another example, the embodiments disclosed herein provide a level sensor with a small form-factor that is agent compatible. Further, by including a combined sensor for measuring both the level of liquid anesthetic agent in the vaporizing chamber and the level of liquid anesthetic agent in the sump, sensor costs may be reduced, thereby decreasing a cost of manufacturing the anesthetic vaporizer. Further, by including the sealing disc on the measurement target in the vaporizing chamber, the inductive level sensor additionally functions as a sealing system to prevent degradation of downstream pneumatic and sensor componentry due to liquid accumulation in the output manifold.

Figure 2:
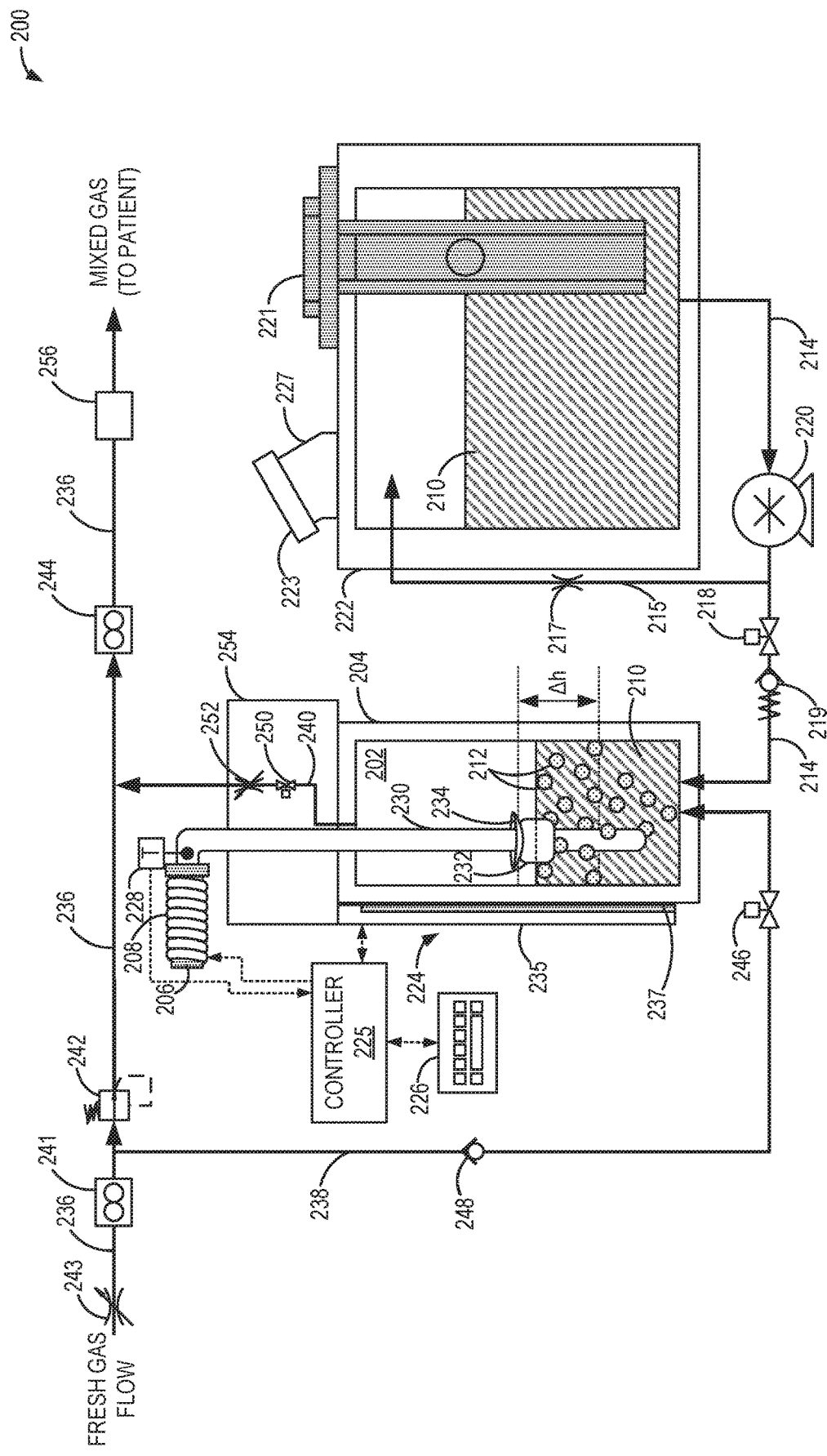
FIG. 2 schematically shows a first exemplary embodiment of an anesthetic vaporizer that may be included in an anesthesia machine.
Figure 3:
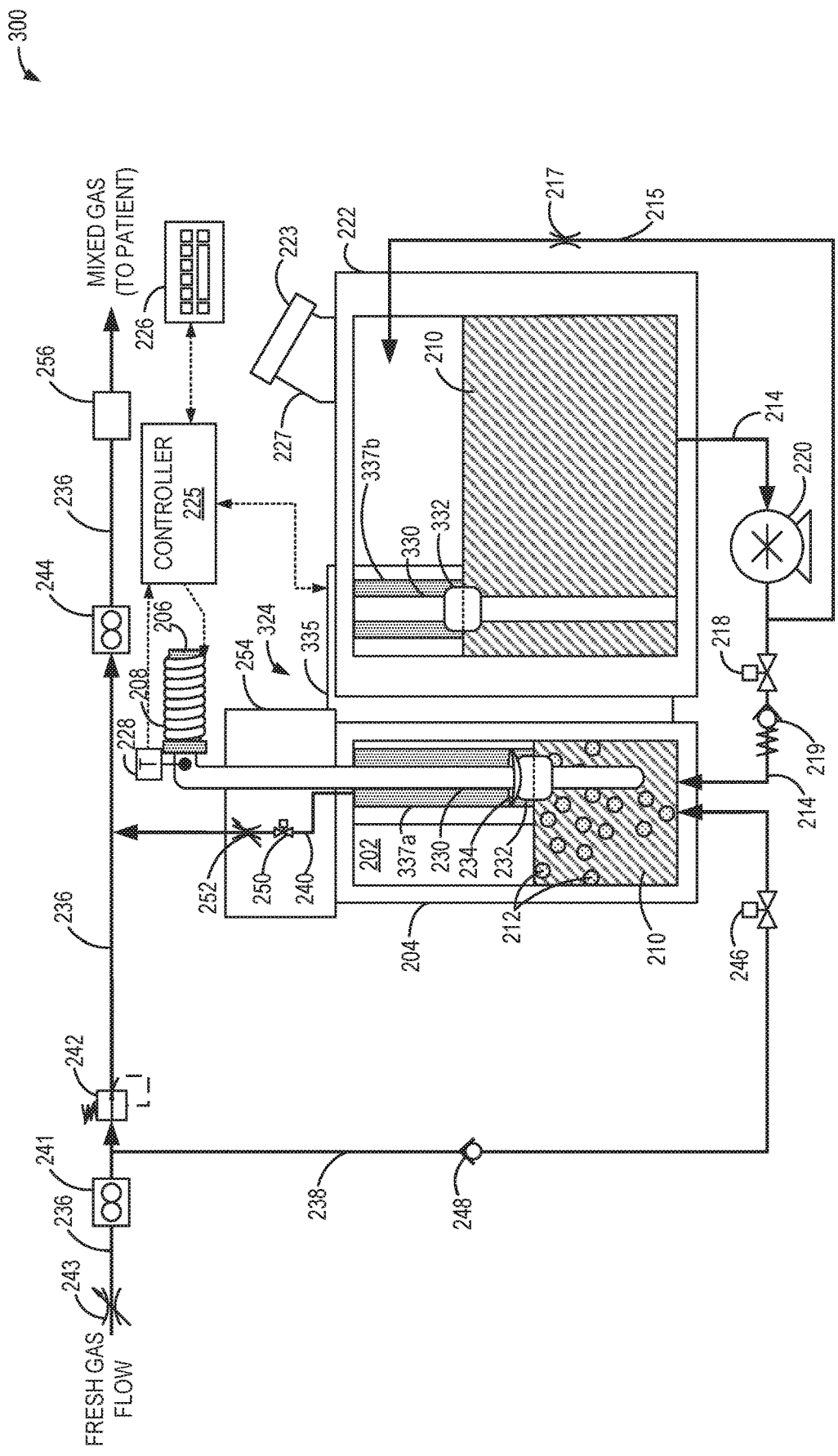
FIG. 3 schematically shows a second exemplary embodiment of an anesthetic vaporizer that may be included in an anesthesia machine.
Figure 4:
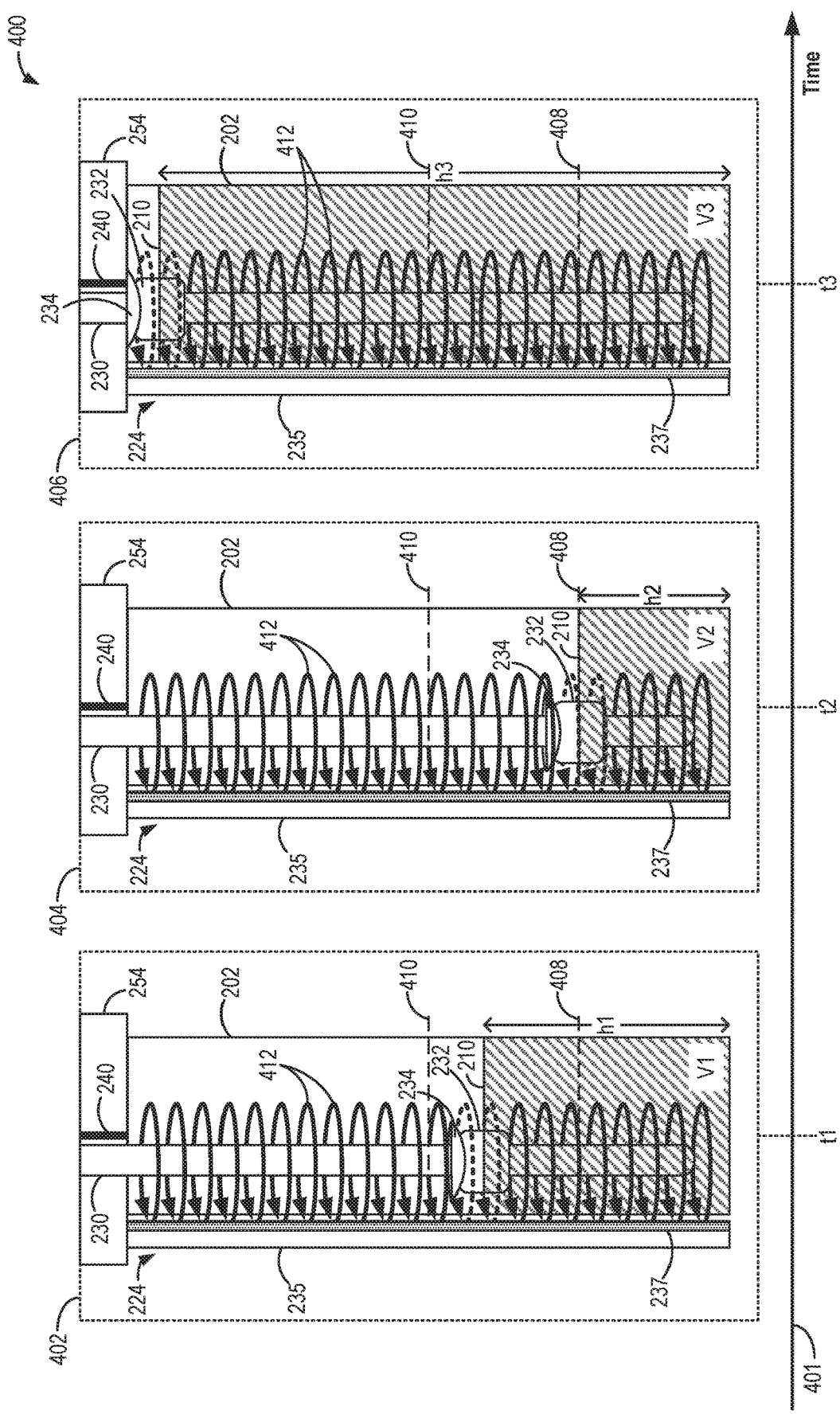
FIG. 4 schematically shows an example timeline for determining a volume of liquid anesthetic agent in a sump via an inductive level sensor.

FIG. 1 schematically shows an exemplary embodiment of an anesthesia machine. FIG. 2 shows a first exemplary embodiment of an anesthetic vaporizer that may be included in the anesthesia machine of FIG. 1, the first embodiment including an inductive level sensor for measuring a level of liquid anesthetic agent in a vaporizing chamber. FIG. 3 shows a second exemplary embodiment of an anesthetic vaporizer that may be included in the anesthesia machine of FIG. 1, the second embodiment including a combined inductive level sensor for measuring both the level of liquid anesthetic agent in the vaporizing chamber and a level of liquid anesthetic agent in a sump that supplies the liquid anesthetic agent to the vaporizing chamber via a pump. FIG. 4 shows an example timeline showing how a level measurement made by the inductive level sensor changes as the level (and volume) of liquid anesthetic agent in the vaporizing chamber changes. A controller may operate the inductive level sensor to measure the level of liquid anesthetic agent in either the sump or the vaporizing chamber according to the example method of FIG. 5. Further, the controller may use the level measurement from the vaporizing chamber to control operation of the pump, such as according the example method of FIG. 6, and may track the volume of liquid anesthetic agent in the sump to alert an operator to refill the sump when a remaining operational time is low, such as according to the example method of FIG. 7. Likewise, given such precision level sensing within the sump, a time-to-empty calculation for the sump is possible given the current, measured volume of anesthetic agent in the sump, a known fresh gas flow rate into the vaporizer, a known output anesthetic agent concentration and the temperature and type of the liquid anesthetic agent. In addition, the level measurements may be used to detect anesthetic agent leakage, such as according to the example method of FIG. 8.

FIG. 1 schematically shows an example anesthesia machine 100. Anesthesia machine 100 includes a frame (or housing) 102. In some embodiments, frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

Anesthesia machine 100 also includes an anesthesia display device 104, a patient monitoring display device 106, a respiratory gas module 108, one or more patient monitoring modules, such as a patient monitoring module 110, a ventilator 112 (explained in more detail below), an anesthetic vaporizer 114, and an anesthetic agent storage bay 116. Anesthesia machine 100 may further include a main power indicator 124, a system activation switch 126 (which, in one example, permits gas flow when activated), an oxygen flush button 128, and an oxygen control 130. Example embodiments of anesthetic vaporizer 114 will be described below with respect to FIGS. 2 and 3. Anesthetic vaporizer 114 may vaporize the anesthetic agent and combine the vaporized anesthetic agent with one or more medical grade gases (e.g., oxygen, air, nitrous oxide, or combinations thereof), which may then be delivered to a patient.

Anesthesia machine 100 may additionally include an integrated suction, an auxiliary oxygen flow control, and various other components for providing and/or controlling a flow of the one or more medical grade gases to the patient. For example, anesthesia machine 100 includes one or more pipeline connections 146 to facilitate coupling of the anesthesia machine to pipeline gas sources. Additionally, anesthesia machine 100 includes a cylinder yoke 144, via which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via the ventilator 112. The anesthesia machine may also include a serial port, a collection bottle connection, a cylinder wrench storage area, and an anesthesia gas scavenging system.

The ventilator 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ventilator 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via the expiratory port 120, where carbon dioxide may be removed from the expiratory gases via the absorber canister.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of anesthesia machine 100. In some embodiments, a first flow control valve may be positioned between the gas source(s) and the anesthetic vaporizer 114 and may be actuatable via the flow adjustment devices to a fully opened position, a fully closed position, and a plurality of positions between the fully opened position and the fully closed position.

Anesthesia machine 100 may additionally include one or more valves configured to bypass gases from the gas source(s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via the inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further, the respiratory gas module 108 may measure respiration rate, minimum alveolar concentration, patient oxygen, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ventilator 112 may optionally be coupled to a breathing circuit (not shown) including a plurality of tubes (e.g., gas passages) 122. The breathing circuit may be coupled between an airway of a patient (e.g., via a breathing mask positioned to enclose the mouth and/or nose of the patient or a tracheal intubation tube) and the inspiratory port 118. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patient (e.g., through inhalation) via the inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 114, the ventilator 112, the respiratory gas module 108, the anesthesia display device 104, and the patient monitoring display device 106.

The controller 140 receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled via an input device (e.g., keyboard, touchscreen, etc.) coupled to the electronic controller of the anesthesia machine 100. The controller 140 may display operating parameters of the anesthesia machine 100 via the anesthesia display device 104 and/or the patient monitoring display device 106. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

Controller 140 is shown in FIG. 1 for illustrative purposes, and it is to be understood that controller 140 may be located in various locations within, around, and/or remote from anesthesia machine 100. As an example, controller 140 may include multiple devices/modules that may be distributed throughout anesthesia machine 100. As such, controller 140 may include a plurality of controllers at various locations within anesthesia machine 100. As another example, additionally or alternatively, controller 140 may include one or more devices/modules that are external to anesthesia machine 100, located proximate to (e.g., in a same room) or remote from (e.g., a remote server) anesthesia machine 100. In each example, the multiple devices/modules may be communicatively coupled through wired and/or wireless connections.

Anesthetic vaporizers, such as anesthetic vaporizer 114 shown in FIG. 1, may employ various vaporizer engines (e.g., liquid to gas conversion components) to vaporize a liquid anesthetic agent. For example, the anesthetic vaporizer may use a flow-over vaporizer engine (in which a carrier gas flows over a top surface of a volatile liquid anesthetic agent), a wick-based vaporizer engine, a bubble-through vaporizer engine (in which the carrier gas is bubbled up through the liquid anesthetic agent), or a gas/vapor blender (in which heat is used to vaporize the liquid anesthetic agent, and the vapors are injected into a fresh gas flow). When the anesthetic agent undergoes a phase change from liquid to vapor, it absorbs energy, known as latent heat of vaporization. Therefore, flow-over, wick-based, and bubble-through vaporizers may also utilize a heating mechanism to provide energy for the latent heat of vaporization, at least in some examples.

FIG. 2 shows a first exemplary embodiment of an anesthetic vaporizer 200, which may be included in an anesthesia machine (e.g., anesthesia machine 100 shown in FIG. 1). As one example, anesthetic vaporizer 200 may be anesthetic vaporizer 114 of FIG. 1. In particular, anesthetic vaporizer 200 is a bubble-through anesthetic vaporizer, including a vaporizing chamber 202 defined by a housing 204. Housing 204 may be comprised of plastic, for example, or another non-metallic material. A lower portion of vaporizing chamber 202 is shown holding a liquid anesthetic agent 210 that is supplied from a sump 222 via a conduit 214 and a pump 220. The liquid anesthetic agent 210 may be isoflurane, sevoflurane, or another liquid anesthetic agent of similar volatility, for example. Pump 220 may be a positive displacement pump, such as a reciprocating positive displacement pump, for example. Pump 220 may be selectively operated to deliver liquid anesthetic agent 210 from sump 222 to vaporizing chamber 202 in response to a command signal from a controller 225, as will be further described below. Controller 225 may be an electronic controller including a processor operatively connected to a memory. Controller 225 may be included in (e.g., a part of) or communicatively coupled to controller 140 shown in FIG. 1, for example.

Sump 222 may be refilled via a fill cap 223 and a fill port (e.g., neck) 227. Together, fill cap 223 and fill port 227 may be included in a fill assembly. For example, an operator of anesthetic vaporizer 200 may remove fill cap 223 to refill sump 222 with additional liquid anesthetic agent 210 (e.g., from a refill bottle) via fill port 227 and then replace fill cap 223 to seal sump 222. Fill cap 223 may be a screw cap, for example. Furthermore, pump 220 may decouple vaporizing chamber 202 from sump 222, enabling sump 222 to be refilled while anesthetic vaporizer 200 is in use. Thus, sump 222 may be a sealed system when fill cap 223 is in place and when pump 220 is off (e.g., deactivated) or on (e.g., activated and operating) and between pump pulses.

Conduit 214 may further include a shut-off valve 218 coupled between pump 220 and vaporizing chamber 202. For example, shut-off valve 218 may be an on-off valve, wherein shut-off valve 218 is actuated to an open (e.g., fully open) position that allows liquid anesthetic agent 210 to flow between sump 222 and pump 220 or a closed (e.g., fully closed) position that prevents (e.g., blocks) the flow of liquid anesthetic agent 210 between pump 220 and vaporizing chamber 202. Shut-off valve 218 may be actuated between the open and closed positions in response to a command signal from controller 225, for example. A liquid return line 215 may be coupled to conduit 214 between shut-off valve 218 and pump 220 to reduce pressure build up between shut-off valve 218 and pump 220, such as when shut-off valve 218 is closed. For example, excess liquid anesthetic agent 210 provided by pump 220 may be returned to sump 222 via liquid return line 215.

Conduit 214 may further include a check valve 219 coupled between shut-off valve 218 and vaporizing chamber 202. Check valve 219 may be a one-way, spring-loaded check valve that allows liquid anesthetic agent 210 to flow from pump 220 through open shut-off valve 218 to vaporizing chamber 202 and prevents liquid anesthetic agent 210 from flowing from vaporizing chamber 202 to pump 220. For example, check valve 219 may open automatically (e.g., without input or adjustment from the controller or operator) to flow the liquid anesthetic agent 210 toward vaporizing chamber 202 and close automatically to prevent the liquid anesthetic agent 210 from flowing from vaporizing chamber 202 back to pump 220. Further, liquid return line 215 may include a restriction 217, such as an orifice, to control flow through liquid return line 215. As a result, liquid anesthetic agent 210 may preferentially flow through check valve 219 instead of restriction 217 when shut-off valve 218 is open.

Controller 225 may selectively activate pump 220 to provide liquid anesthetic agent 210 from sump 222 to vaporizing chamber 202 responsive to a measurement received from an inductive level sensor 224 configured to measure a level of liquid anesthetic agent 210 in vaporizing chamber 202. Inductive level sensor 224 is a non-contact level sensor, including a circuit board 235 external to vaporizing chamber 202 (e.g., external to housing 204) that includes an inductive coil strip 237. Inductive coil strip 237 may include two coil types, such as transmitter coils and receiver coils, that are etched and/or printed onto a surface of circuit board 235 that is nearest and parallel to a sidewall of housing 204. As will be further illustrated with respect to FIG. 3, the inductive coil strip 237 may be aligned with a float 232 that is interior to vaporing chamber 202, where the float 232 is a measurement target of level sensor 224. Float 232 is less dense than liquid anesthetic agent 210 and includes a core having metallic plating on a surface of the core. For example, the core may be comprised of one or more of polypropylene, nylon, and ultrahigh molecular weight polyethylene, and the metallic plating may be comprised of one or more of nickel, brass, and stainless steel.

Float 232 is positioned around a rod and is configured to slide vertically along a length of the rod. For example, float 232 may form a ring around heat pipe 230. In the example of FIG. 2, a portion of a heat pipe 230 that extends into vaporizing chamber 202 comprises the rod. Heat pipe 230 is configured to supply heat for converting liquid anesthetic agent 210 into agent vapor, as will be elaborated below. Float 232 has a central cylindrical opening with an inner diameter that is slightly greater than an outer diameter of heat pipe 230, allowing float 232 to slide vertically and rotate around heat pipe 230 without appreciably moving in the horizontal directions. As shown in FIG. 2, the buoyant float 232 sits on or at a surface of the liquid anesthetic agent 210 within vaporizing chamber 202, and thus, as a vertical height (e.g., level) of the liquid anesthetic agent 210 within vaporizing chamber 202 changes, the vertical position of float 232 on heat pipe 230 changes. In some embodiments, such as the embodiment shown in FIG. 2, heat pipe 230 may not extend to a bottom interior surface of vaporizing chamber 202, but a distance between the bottom of heat pipe 230 and the bottom interior surface of vaporizing chamber 202 may be such that float 232 may not dismount heat pipe 230. By including heat pipe 230 as a dual function heat delivery component and level sensor component, manufacturing costs and/or packaging space may be reduced.

This change in height is detected by the receiver coils of inductive coil strip 237, as will be illustrated with respect to FIG. 4. Controller 225 may be electronically connected to inductive coil strip 237 via a chip included on circuit board 235, for example. For example, controller 225 may activate the transmitter coils of inductive coil strip 237, such as by flowing electric current through the transmitter coils, to generate a magnetic field. The metallic plating on float 232 attenuates the magnetic field at the specific vertical location of float 232, and thus the vertical height of the liquid anesthetic agent 210 in vaporizing chamber 202. By positioning float 232 around heat pipe 230, movement of float 232 is constrained in the horizontal directions, ensuring that float 232 is a consistent horizontal distance from inductive coil strip 237 and therefore produces a consistent magnetic field attenuation. Further, housing 204 may not interact with the magnetic field. The receiver coils of inductive coil strip 237 are configured to sense changes in the magnetic field generated by the transmitter coils of inductive coil strip 237. For example, a current flowing through the receiver coils at the specific vertical location of float 232 may change in response to the attenuated magnetic field. Thus, controller 225 may determine the vertical location of float 232, and thus the level of liquid anesthetic agent 210 in vaporizing chamber 202, based on output from the receiver coils of inductive coil strip 237. Further, a geometry of float 232 and a thickness of the metallic plating on the float may be optimized to maximize an effect on the transmitted magnetic field and the resulting signal output by the receiver coils, thereby increasing sensitivity to the float position with respect to inductive coil strip 237.

In one embodiment, controller 225 may be configured to maintain the level of liquid anesthetic agent 210 within vaporizing chamber 202 within a threshold range $\Delta h$ based on the output received from inductive level sensor 224. The threshold range $\Delta h$ may be defined by a first, lower threshold level and a second, higher threshold level. The first threshold level may be a pre-determined, non-zero level of the liquid anesthetic agent that is calibrated to maintain a minimum level of liquid anesthetic agent 210 in vaporizing chamber 202 for desired vaporization properties. As one non-limiting example, the first threshold may correspond to one quarter of a total capacity of vaporizing chamber 202. The second threshold level may be a pre-determined, non-zero level of the liquid anesthetic agent that is calibrated to prevent overfilling of vaporizing chamber 202 with liquid anesthetic agent 210 and minimize variation in the desired vaporization properties throughout the threshold range. As one non-limiting example, the second threshold may correspond to one half of the total capacity of vaporizing chamber 202. As will be elaborated below with respect to FIG. 6, in one embodiment, controller 225 may adjust a duty cycle of activation of pump 220 based on the level measured by inductive level sensor 224 in order to maintain the level of liquid anesthetic agent 210 within vaporizing chamber 202 between the first threshold and the second threshold. In some embodiments, controller 225 may additionally or alternatively activate pump 220 in response to the level of anesthetic agent 210 reaching the first, lower threshold level and deactivate pump 220 responsive to the level of anesthetic agent 210 reaching the second, higher threshold level.

In some embodiments, pump 220 may include a positive displacement stepper motor, where each positive displacement step of the pump is equivalent to a specified volume of anesthetic liquid. In this manner, the pump can be used to precisely fill the vaporization chamber and prevent overfill by recording the number of pump steps delivered. This approach may also be used to record a volume of liquid anesthetic agent 210 delivered to the vaporizing chamber 202, which may be used for anesthetic vaporizer run-time/maintenance analysis (service metrics), liquid leak detection, precise determination of amount of liquid anesthetic remaining and available for delivery, vaporization efficiency calculations, etc.

An upper portion of vaporizing chamber 202 (e.g., above a surface of liquid anesthetic 210) holds vapor, which may be a mixture of vaporized anesthetic agent and a carrier gas from a fresh gas flow. The fresh gas flow, and thus the carrier gas, may include one or more medical grade gases, such as oxygen, air, nitrous oxide, and combinations thereof. The fresh gas flow may be provided via one or more gas pipelines (e.g., via pipeline connections 416 shown in FIG. 1) and/or one or more gas-holding cylinders (e.g., via cylinder yoke 144 of FIG. 1). As shown in FIG. 2, the fresh gas flow may enter the anesthetic vaporizer 200 via a first gas passage 236. A first proportional valve 243 coupled to the first gas passage 236 may be adjusted by controller 225 to control an amount (or flow rate) of fresh gas flowing through the first gas passage 236. First proportional valve 243 may be a variable valve, such a continuously variable valve, that may be adjusted by controller 225 between a plurality of positions ranging from a fully open to a fully closed position. For example, as a degree of opening of first proportional valve 243 increases, an amount (e.g., flow rate) of fresh gas flowing through first gas passage 236 may increase.

A first mass flow sensor 241 may be coupled to first gas passage 236 downstream of first proportional valve 243 to measure a flow rate of the fresh gas flow entering the anesthetic vaporizer 200. For example, first mass flow sensor 241 may be an ultrasonic flow meter or a calorimetric (thermal) mass flow meter. A pressure regulator 242 coupled to first gas passage 236 may limit a pressure of the fresh gas flow downstream of pressure regulator 242. For example, pressure regulator 242 may be a pressure reducing valve such that a pressure of the fresh gas flow downstream of pressure regulator 242 does not exceed a pressure setpoint of the pressure regulator. Further, first mass flow sensor 241 may be used by controller 225 as part of the control system to provide feedforward control information upon a change in fresh gas flow into anesthetic vaporizer 200.

A second gas passage 238 branches off of the first gas passage between first mass flow sensor 241 and pressure reducing valve 242 to provide carrier gas (e.g., a portion of the fresh gas flow that flows to vaporizing chamber 202) to vaporizing chamber 202. For example, second gas passage 238 may pass through an opening in the bottom of housing 204, which may include a gas-tight seal, to flow the carrier into the liquid anesthetic agent 210 within vaporizing chamber 202. Thus, second gas passage 238 may serve as a gas inlet passage to vaporizing chamber 202. Further, pressure regulator 242 may control a gas pressure within second gas passage 238.

Second gas passage 238 may include one or more valves disposed therein. As shown in FIG. 2, second gas passage 238 includes a check valve 248 and a shut-off valve 246. Check valve 248 may be a one-way valve that allows the carrier gas to flow from the fresh gas flow to vaporizing chamber 202 and prevents the carrier gas from flowing from vaporizing chamber 202 toward first gas passage 236. For example, check valve 248 may open automatically (e.g., without input or adjustment from a controller or operator) to flow the carrier gas through second gas passage 238 toward vaporizing chamber 202 and close automatically to prevent gas flow toward first gas passage 236. In contrast, shut-off valve 246 may be an electronically or mechanically actuated valve that is operated responsive to input from controller 225 and/or an operator of anesthetic vaporizer 200 (e.g., an anesthesiologist). For example, shut-off valve 246 may be an on-off valve, where shut-off valve 246 is actuated to an open (e.g., fully open) position that allows gas flow through shut-off valve 246 or a closed (e.g., fully closed) position that prevents (e.g., blocks) gas flow through shut-off valve 246 in response to an appropriate command signal from controller 225.

The carrier gas delivered via second gas passage 238 flows through into vaporizing chamber 202 at or near the bottom of housing 204 to form a plurality of gas bubbles 212 within liquid anesthetic agent 210. The plurality of gas bubbles 212 pass through liquid anesthetic agent 210, becoming saturated with anesthetic agent as they rise to the surface of the liquid via mass transport of agent into the bubble. Vaporization of the liquid anesthetic agent is affected by bubble size, an amount of time the gas bubbles 212 spend in the liquid anesthetic agent 210 (which may be controlled for by controlling the level of the liquid anesthetic agent 210 in vaporizing chamber 202, as described above), and a temperature difference between each gas bubble 212 and the liquid anesthetic agent 210. Therefore, anesthetic vaporizer 200 includes heat pipe 230 for providing heat to vaporizing chamber 202. Further, float 232 positioned on heat pipe 230 may dampen bubbling through the liquid anesthetic agent 210 within vaporizing chamber 202, thereby reducing sloshing.

Heat pipe 230 is partially disposed within vaporizing chamber 202. In the embodiment illustrated in FIG. 2, heat pipe 230 is bent (e.g., by approximately 90°) so that a first, horizontal portion of heat pipe 230 is external to vaporizing chamber 202. A second, vertical portion of heat pipe 230 extends through a manifold 254 and an opening in the top of housing 204 (which may include a gas-tight seal, for example) and into vaporizing chamber 202. In some embodiments, the horizontal portion of heat pipe 230 may be positioned in a gas-tight barrier that may isolate the components therein from vaporizing chamber 202, for example. In other embodiments, heat pipe 230 may extend into vaporizing chamber 202 through the bottom of housing 204. Thus, the positioning shown in FIG. 2 of heat pipe 230 relative to vaporizing chamber 202 is provided by way of example.

In the embodiment illustrated in FIG. 2, a bottom of the vertical portion of heat pipe 230 is submerged within the liquid anesthetic agent 210 held in vaporizing chamber 202. Thus, the vertical portion of heat pipe 230 is at least partially submerged within the liquid anesthetic agent 210. Heat pipe 230 may be comprised of copper or nickel plated copper, for example, or another material having a high thermal conductivity and low magnetism. The horizontal portion of heat pipe 230 may be in direct contact with a ferromagnetic collar 206. In one embodiment, the horizontal portion of heat pipe 230 is friction-fit within ferromagnetic collar 206. Ferromagnetic collar 206 may be a thin-walled collar comprised of 400 series stainless steel, various grades of highly magnetic steel, iron, or other ferromagnetic materials (note that non-ferromagnetic materials can be used but at a substantially lower efficiency). A heating element 208 is positioned external to vaporizing chamber 202 and may be coiled around a length of ferromagnetic collar 206, as shown. Further, heating element 208 may be in direct contact with (e.g., touching) ferromagnetic collar 206 or may not be in direct contact with ferromagnetic collar 206. In the embodiment of FIG. 2, heating element 208 is an induction heater including a power source, a high-current inductive heating coil, and an electronic oscillator that passes a high frequency (e.g., ~50 kHz) alternating current through the coil, creating a rapidly alternating magnetic field. The rapidly alternating magnetic field produced by heating element 208 penetrates ferromagnetic collar 206, generating eddy currents within ferromagnetic collar 206 to heat it via Joule heating and magnetic hysteresis losses. In this way, heating element 208 may selectively heat ferromagnetic collar 206 via induction heating without becoming hot itself and/or without directly heating additional components of anesthetic vaporizer 200 (e.g., heat pipe 230).

Induction heating of ferromagnetic collar 206 by heating element 208 may provide several advantages. For example, the heat is generated inside the ferromagnetic collar itself instead of via an external heat source via conduction. Thus, ferromagnetic collar 206 may be rapidly heated once heating element 208 is activated. Further, heating element 208 need not be in direct contact with ferromagnetic collar 206, reducing contamination between components. However, in other embodiments, heating element 208 may heat through conduction, and thus heating element 208 may be in direct contact with ferromagnetic collar 206 for efficient heat transfer.

As heat is generated within ferromagnetic collar 206 during the induction heating, the heat may be efficiently transferred to heat pipe 230 via conduction. Thus, selectively heating ferromagnetic collar 206 via induction heating by heating element 208 may also selectively heat the heat pipe 230. Heat pipe 230 transports the generated heat along its length such that a temperature of the entire heat pipe is substantially the same, and the temperature of the heat pipe is substantially the same as a temperature of ferromagnetic collar 206. In this way, the heat generated by the induction heating of ferromagnetic collar 206 by heating element 208 reaches vaporizing chamber 202 and the liquid anesthetic agent 210 contained therein to provide the latent heat of vaporization for the phase transition to the vapor form.

In one embodiment, controller 225 may adjust the amount of heat generated (e.g., via induction heating) to control an amount of vaporized anesthetic agent generated at vaporizing chamber 202. As an example, when a desired anesthetic agent flow rate (or concentration) to deliver to a patient is low, an amount of power provided to heating element 208 may be lower, preventing cool off from the latent heat of vaporization without increasing a temperature of the liquid anesthetic agent 210 and/or the gas bubbles 212. As another example, when the desired anesthetic agent flow rate (or concentration) is high, the amount of power provided to heating element 208 may be higher to facilitate production of additional vapor bubbles, such as through nucleated boiling off of the surface of heat pipe 230. Thus, all of the carrier gas that flows through vaporizing chamber 202 may be fully saturated with vapor from liquid anesthetic agent 210, even at high fresh gas flow rates (e.g., 10 L/min).

Vapor, such as the carrier gas that is saturated with vaporized anesthetic agent, may flow out of vaporizing chamber 202 via a third gas passage 240 (e.g., a vapor delivery passage). For example, third gas passage 240 may pass through an opening at or near a top of housing 204 and form a junction with first gas passage 236 to fluidically couple the upper portion of vaporizing chamber 202 with first gas passage 236. Third gas passage 240 is shown including a shut-off valve 250 and a second proportional valve 252 within manifold 254, which may be coupled to a top surface of housing 204. Shut-off valve 250 may be an electronically or mechanically actuated valve that is adjusted responsive to input from controller 225 and/or the operator. For example, shut-off valve 250 may be an on-off valve, wherein shut-off valve 250 is actuated to an open (e.g., fully open) position that allows gas flow through shut-off valve 250 or a closed (e.g., fully closed) position that prevents (e.g., blocks) gas flow through shut-off valve 250 in response to an appropriate command signal from controller 225. Shut-off valve 250 may be closed to quickly stop the supply of the anesthetic agent to a patient, for example. Second proportional valve 252 may be a variable valve, such a continuously variable valve, that may be adjusted by controller 225 between a plurality of positions ranging from a fully open to a fully closed position. For example, as a degree of opening of second proportional valve 252 increases, an amount (e.g., flow rate) of vapor flowing from vaporizing chamber 202 to first gas passage 236 (e.g., via third gas passage 240) may increase. Conversely, as the degree of opening of second proportional valve 252 decreases, the amount of vapor delivered from vaporizing chamber 202 to first gas passage 236 may decrease.

In the exemplary embodiment shown in FIG. 2, heat pipe 230 passes through manifold 254 on its way to vaporizing chamber 202. Thus, heat pipe 230 may additionally heat manifold 254 to prevent condensation of the vaporized anesthetic agent in shut-off valve 250 and second proportional valve 252. However, in other embodiments, manifold 254 may additionally or alternatively be heated by a dedicated manifold heater to maintain the valves at a substantially constant temperature, such as 40° C. in one non-limiting example.

Further, as described above, float 232 is configured to move vertically along heat pipe 230 based on the level of liquid anesthetic agent 210 in vaporizing chamber 202. Thus, heat pipe 230 may advantageously serve two functions: to provide heat to liquid anesthetic agent 210 in vaporizing chamber 202 and to provide the rod for float 232. However, in other embodiments, heat may be provided to liquid anesthetic agent 210 in vaporizing chamber 202 without a heat pipe, such as via a conductive heating element coupled to housing 204, and float 232 may then be positioned on a rod that does not function as a heat pipe.

In some embodiments, a sealing disc 234 is positioned on and coupled to a top surface of float 232 to prevent liquid anesthetic agent 210 from reaching manifold 254 and the valves disposed therein (e.g., shut-off valve 250 and second proportional valve 252). Sealing disc 234 may be comprised of an elastomeric material, such as soft plastic, ethylene propylene diene monomer rubber, silicone rubber, etc., that may deform to plug the opening to third gas passage 240 and then return to its original (e.g., non-deformed) shape. For example, degradation of the control of pump 220 may cause overfilling of vaporizing chamber 202. Therefore, when the liquid anesthetic agent level gets high enough, sealing disc 234 may press against the interior surface of the top of housing 204, forming a liquid-tight seal with the opening to third gas passage 240. Thus, float 232 may advantageously serve two functions: to provide an inductive measurement target for measuring the level of liquid anesthetic agent 210 within vaporizing chamber 202 and to press sealing disc 234 into the opening to third gas passage 240 during an overfilling condition. Further, the dampening action provided by float 232 may reduce sloshing of liquid anesthetic agent into third gas passage 240 even when an overfilling condition is not present. As liquid anesthetic agent 210 may degrade second proportional valve 252 and shut-off valve 250, preventing liquid accumulation within manifold 254 may reduce second proportional valve 252 and shut-off valve 250 degradation. Additionally, when liquid anesthetic agent 210 reaches manifold 254, a concentration of anesthetic agent provided to the patient may not be accurately controlled. Therefore, reducing liquid accumulation within manifold 254 by dampening bubbling via float 232 and sealing the opening to third gas passage 240 during an overfilling condition via sealing disc 234 may prevent anesthetic agent dosing inaccuracies.

Upstream of the junction with third gas passage 240 and downstream of the junction with second gas passage 238, first gas passage 236 carries a portion of the fresh gas flow called bypass gas. The bypass gas does not pass through vaporizing chamber 202. An amount of bypass gas flowing through first gas passage 236 may be adjusted by adjusting the fresh gas flow and may be limited by pressure regulator 242. The bypass gas, containing no vaporized anesthetic agent, and the vapor from vaporizing chamber 202, containing the carrier gas saturated with the vaporized anesthetic agent, mix at and downstream of the junction between first gas passage 236 and third gas passage 240. The mixed gas may then be delivered to the patient via an inspiratory limb of a breathing circuit (e.g., via inspiratory port 118 described with respect to FIG. 1). A second mass flow sensor 244 may be coupled to first gas passage 236 downstream of the junction with third gas passage 240 to measure a flow rate of the mixed gas exiting the anesthetic vaporizer 200. For example, second mass flow sensor 244 may be an ultrasonic flow meter or a calorimetric (thermal) mass flow meter. In the case of an ultrasonic flow metering architecture, the output anesthetic agent concentration may be calculated by the difference in the measured time of flight (ToF) between the upstream first mass flow sensor 241 and the downstream second mass flow sensor 244.

Further, in some embodiments, an independent concentration sensor 256 may be coupled to first gas passage 236 downstream of the junction with third gas passage 240. Concentration sensor 256 may be any suitable sensor that is configured to measure a concentration of the anesthetic agent in the mixed gas. In one example, concentration sensor 256 may be an optical sensor that transmits light of a suitable wavelength (e.g., infrared) through the mixed gas and determines a concentration of the anesthetic agent based on an absorption of the light by the mixed gas. In other examples, the concentration sensor may be an oxygen sensor that measures the concentration of the anesthetic agent based on a displacement of the oxygen relative to a supplied concentration of oxygen in the fresh gas flow. Concentration sensor 256 may output a signal to controller 225 indicative of the measured concentration of the anesthetic agent (e.g., the concentration of the anesthetic agent vapor) in the mixed gas. Additionally, ultrasound may be used to measure a change in the gas speed of sound prior to and after introduction of vaporized anesthetic agent into the gas stream. The change in the speed of sound is a function of the anesthetic agent concentration, and thus, ultrasound may be used to determine the concentration of the anesthetic agent in the mixed gas.

In addition to receiving signals output by inductive level sensor 224, concentration sensor 256, first mass flow sensor 241, and second mass flow sensor 244, controller 225 may receive additional signals, including a measured level of liquid anesthetic agent 210 within sump 222 from a level sensor 221, which may be an optical level sensor (as shown), an inductive level sensor (similar to inductive level sensor 224), an ultrasonic level sensor, or any other type of continuous liquid level sensor. Further, controller 225 may receive a measured temperature of heat pipe 230 from a temperature sensor 228 coupled to heat pipe 230 external to vaporizing chamber 202. The measured temperature of heat pipe 230 may give an indication of the temperature of the liquid anesthetic agent 210 within vaporizing chamber 202 in order to avoid overheating of the liquid anesthetic agent. In some embodiments, anesthetic vaporizer 200 may additionally or alternatively include a separate liquid anesthetic agent temperature sensor. Additional sensors may be positioned throughout anesthetic vaporizer 200, such as various pressure, temperature, and/or composition sensors.

Controller 225 receives the signals from the various sensors of FIG. 2, processes the input data, and employs the various actuators of FIG. 2 to adjust operation of anesthetic vaporizer 200 based on the received signals and instructions stored on a memory of the controller. For example, controller 225 may receive the measured concentration of the anesthetic agent from concentration sensor 256 and adjust a position of one or more of the first proportional valve 243 and the second proportional valve 252. As another example, controller 225 may receive the temperature of heat pipe 230 from temperature sensor 228 and adjust operation of heating element 208 based on the input measurements. In still another example, controller 225 may receive a measurement of level of liquid anesthetic agent 210 in vaporizing chamber 202 from inductive level sensor 224 and adjust operation of pump 220 based on the received measurement, as will be further described below with respect to FIG. 6.

Further, data may be input to controller 225 by the operator of anesthetic vaporizer 200 via a human-machine interface (HMI) 226 that is operationally connected to the controller (e.g., via wired or wireless communication). HMI 226 may include both a user input device and an output device. The user input device may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator. The output device may include one or more of a display (e.g., anesthesia display device 104 and/or patient monitoring display device 106 of FIG. 1) for providing visual alerts or text-based messages and a speaker for providing audible alerts or messages.

Note that although one controller 225 is shown, controller 225 may include multiple devices/modules distributed at various locations within anesthetic vaporizer 200. As another example, additionally or alternatively, controller 225 may include one or more devices/modules that are external to anesthetic vaporizer 200. In each example, the multiple devices/modules may be communicatively coupled through wired and/or wireless connections.

Anesthetic vaporizer 200 of FIG. 2 includes separate level sensing systems for measuring a level of liquid anesthetic agent 210 in vaporizing chamber 202 and sump 222 (inductive level sensor 224 and level sensor 221, respectively). However, including separate level sensing systems may increase anesthetic vaporizer costs. Therefore, turning now to FIG. 3, a second exemplary embodiment of an anesthetic vaporizer 300 is shown, which may be installed in an anesthesia machine (e.g., anesthesia machine 100 shown in FIG. 1). Except for the differences described below, anesthetic vaporizer 300 may be substantially identical to anesthetic vaporizer 200 of FIG. 2. As such, components previously introduced in FIG. 2 are represented with the same reference numbers and are not re-introduced. Further, although FIG. 3 shows the relative arrangement of some components differently, note that the connectivity of the components and their functionality have not changed, and other relative arrangements may also be possible.

Anesthetic vaporizer 300 includes a combined inductive level sensor 324 that may simultaneously measure both the level of liquid anesthetic agent 210 in vaporizing chamber 202 and the level of liquid anesthetic agent 210 in sump 222. Combined inductive level sensor 324 includes (first) float 232 positioned around the lower, vertical portion of heat pipe 230, as in anesthetic vaporizer 200 of FIG. 2, and additionally includes a second float 332 positioned around a rod 330 within sump 222. In the embodiment shown in FIG. 3, rod 330 extends across a length of sump 222, from a top interior surface to a bottom interior surface of sump 222. Thus, rod 330 may be coupled (e.g., secured) to both the top interior surface of the sump and the bottom interior surface of the sump. However, in other embodiments, rod 330 may be coupled to the top interior surface and not the bottom interior surface or the bottom interior surface and not the top interior surface, but the length of rod 330 may be such that second float 332 cannot dismount from the rod.

Second float 332 may function the same as float 232 for level sensing. However, second float 332 does not include a sealing disc coupled on its top surface, as sump 332 is sealed. Rod 330 may be comprised of one or more non-magnetic metals and metal alloys, such as aluminum, copper, brass, and bronze. Rod 330 may additionally or alternative be comprised of one or more non-metallic, anesthetic agent-compatible materials, such as polypropylene, polyethylene, various other plastics, nylon, and glass.

Combined inductive level sensor 324 further includes a circuit board 335 that includes a first inductive coil strip 337a and a second inductive coil strip 337b printed and/or etched thereon. First inductive coil strip 337a and second inductive coil strip 337b each include transmitter and receiver coils that function independently from the transmitter and receiver coils of the other strip. Circuit board 335 is positioned intermediate vaporizing chamber 202 and sump 222, having a length and height that extends parallel to a length and height of each of the vaporizing chamber and the sump. However, in other embodiments, first inductive coil strip 337a and second inductive coil strip 337b may be positioned on separate circuit boards.

First inductive coil strip 337a is positioned to sense magnetic field changes produced by float 232, and second inductive coil strip 337b is positioned to sense magnetic field changes produced by second float 332. That is, a horizontal position of first inductive coil strip 337a overlaps with a horizontal position of float 232, and a length of first inductive coil strip 337a overlaps with a vertical travel range of float 232. Similarly, a horizontal position of second inductive coil strip 337b overlaps with a horizontal position of second float 332, and a length of second inductive coil strip 337b overlaps with a vertical travel range of second float 332. Further, first inductive coil strip 337a does not overlap with second float 332, and second inductive coil strip 337b does not overlap with float 232. Because a strength of a magnetic field produced by the transmitter coils of either first inductive coil strip 337a or second inductive coil strip 337b drops proportionally to the square of a radial distance from the coil, float 232 may not interact with the magnetic field generated by second inductive coil strip 337b, and second float 332 may not interact with the magnetic field generated by first inductive coil strip 337a.

Controller 225 may actuate the transmitter coils of first inductive coil strip 337a and the transmitter coils of second inductive coil strip 337b independently (e.g., via separate command signals) or together (e.g., via a same command signal). Controller 225 may receive separate output signals from circuit board 335 regarding the level of anesthetic agent 210 measured by the receiver coils of first inductive coil strip 337a and the receiver coils of second inductive coil strip 337b. For example, controller 225 may receive a first signal output from the receiver coils of first inductive coil strip 337a and determine the level of anesthetic agent 210 in vaporizing chamber 202, and controller 225 may receive a second signal output from the receiver coils of second inductive coil strip 337b, separate from the first signal output, and determine the level of liquid anesthetic agent 210 in sump 222. Thus, combined inductive level sensor 324 may produce independent level measurements of the liquid anesthetic agent 210 level in vaporizing chamber 202 and sump 222. Further, controller 225 may take different actions based on whether the received measurement is the level of liquid anesthetic agent 210 in vaporizing chamber 202 or sump 222, as will be described with respect to FIGS. 5-7. In addition, if the volume of liquid drained and transferred between the sump (derived from the sump level sensor during pump actuation) does not match the liquid level increase in the vaporization chamber after (or during) the pumping, a leak between the sump and the vaporizing chamber may be detected.

Next, FIG. 4 schematically shows an example timeline 400 illustrating usage of an inductive level sensor for determining an anesthetic agent level in an anesthetic vaporizer. The anesthetic vaporizer may be anesthetic vaporizer 200 introduced in FIG. 2, including inductive level sensor 224, that receives liquid anesthetic agent 210 from sump 222 (not shown in FIG. 4). As such, components of FIG. 4 that function the same as components previously introduced in FIG. 2 are numbered the same and may not be reintroduced. Further, some components of anesthetic vaporizer 200 are not shown in the example of timeline 400 for simplicity, although it may be understood that such components are present. It may also be understood that combined level sensor 324 of FIG. 3 may function similarly. Controller 225 (not shown in FIG. 4) may execute one or more methods to operate level sensor 224, such as the example method described below with respect to FIG. 5.

Timeline 400 shows a plurality of "snapshots," each representing an instantaneous depiction of an amount (e.g., volume and height) of liquid anesthetic agent 210 within vaporizing chamber 202 at the corresponding time, including a first snapshot 402 at a first time t1, a second snapshot 404 at a second time t2, and a third snapshot 406 at a third time t3. The first time is the earliest time and the third time is the latest time, as shown by a direction of a time axis 401. In particular, each snapshot shows how float 232 vertically moves with a changing level of liquid anesthetic agent 210 within vaporizing chamber 202 and the resulting changes in the level measured by inductive level sensor 224. Further, in the illustrative example of timeline 400, the controller executes a pump control method (e.g., to control pump 220 of FIG. 2) to maintain the liquid anesthetic agent 210 in vaporizing chamber 202 between a first, lower threshold 408 and a second, higher threshold 410.

First snapshot 402 shows float 232 floating on a surface of liquid anesthetic agent 210 having a first height h1. First height h1, and thus the vertical position of float 232 on heat pipe 230, is between the first threshold 408 and the second threshold 410. The controller actuates the transmitter coils of inductive coil strip 237 to generate a magnetic field 412, represented by curved arrows that extend along a length of inductive coil strip 237. Magnetic field 412 substantially surrounds the vertical portion of heat pipe 230 within vaporizing chamber 230 and float 232 positioned thereon and is received by the receiver coils of inductive coil strip 237. Magnetic field 412 is attenuated at the vertical position of float 232, as shown by dashed arrows. Therefore, based on attenuated output by the receiver coils at the vertical position overlapping with float 232, the controller determines liquid anesthetic agent 210 has the first height h1 at time t1. Further, the controller may calculate a first volume V1 based on the first height h1, such as by inputting the first height into a look-up table, function, or graph stored in memory that relates a measured height (e.g., level) to the corresponding volume. The relationship between the level and the volume may be different for different vaporizing chamber geometries; for example, a same measured level may result in a larger volume calculation when the vaporizing chamber is wider than when the vaporizing chamber is narrower.

In the example of timeline 400, the controller maintains the pump deactivated at time t1 because the first height h1 is between the first threshold 408 and the second threshold 410. By maintaining the pump deactivated, power consumption may be reduced and a lifespan of the pump may be increased. However, other pump logics are also possible, such as will be described below with respect to FIG. 6.

Between time t1 and time t2, the anesthetic vaporizer is operated to deliver anesthetic agent to a patient. As shown in second snapshot 404, a vertical height of the float 232 decreases with the vertical height of liquid anesthetic agent 210. Float 232 has a second height h2 from a bottom interior surface of vaporizing chamber 202, which is less than first height h1 at time t1. The vertical position of the attenuated magnetic field 412 also decreases. Therefore, based on the lower attenuated output by the receiver coils, the controller determines liquid anesthetic agent 210 has the second height h2 at time t2 and calculates a second, lower volume V2. Further, the controller recognizes that the second height h2 is equal to the first threshold 408. In response, the controller activates the pump to refill vaporizing chamber 202 until the level of liquid anesthetic agent 210 reaches second threshold 410.

Between time t2 and time t3, the pump control becomes degraded, and the pump continues to deliver liquid anesthetic agent 210 to vaporizing chamber 202 even after the level surpasses second threshold 410. Float 232 continues to rise with the rising level. Third snapshot 406 at time t3 shows liquid anesthetic agent 210 having a third height h3, which is greater than the second threshold 410. The third height h3 is high enough that float 232 presses sealing disc 234 into the top interior surface of vaporizing chamber 202, sealing the opening to third gas passage 240 in manifold 254. In this way, inductive level sensor 224 prevents liquid anesthetic agent 254 from reaching manifold 254 and the components therein even while the pump continues to cycle.

Note that in other examples, the overfilling condition may occur due to degradation of inductive level sensor 224 itself. However, due to the buoyancy of float 232, sealing disc 234 is configured to seal the opening to third gas passage 240 regardless of any level measurement made by level sensor 224 or a lack thereof.

Figure 5:
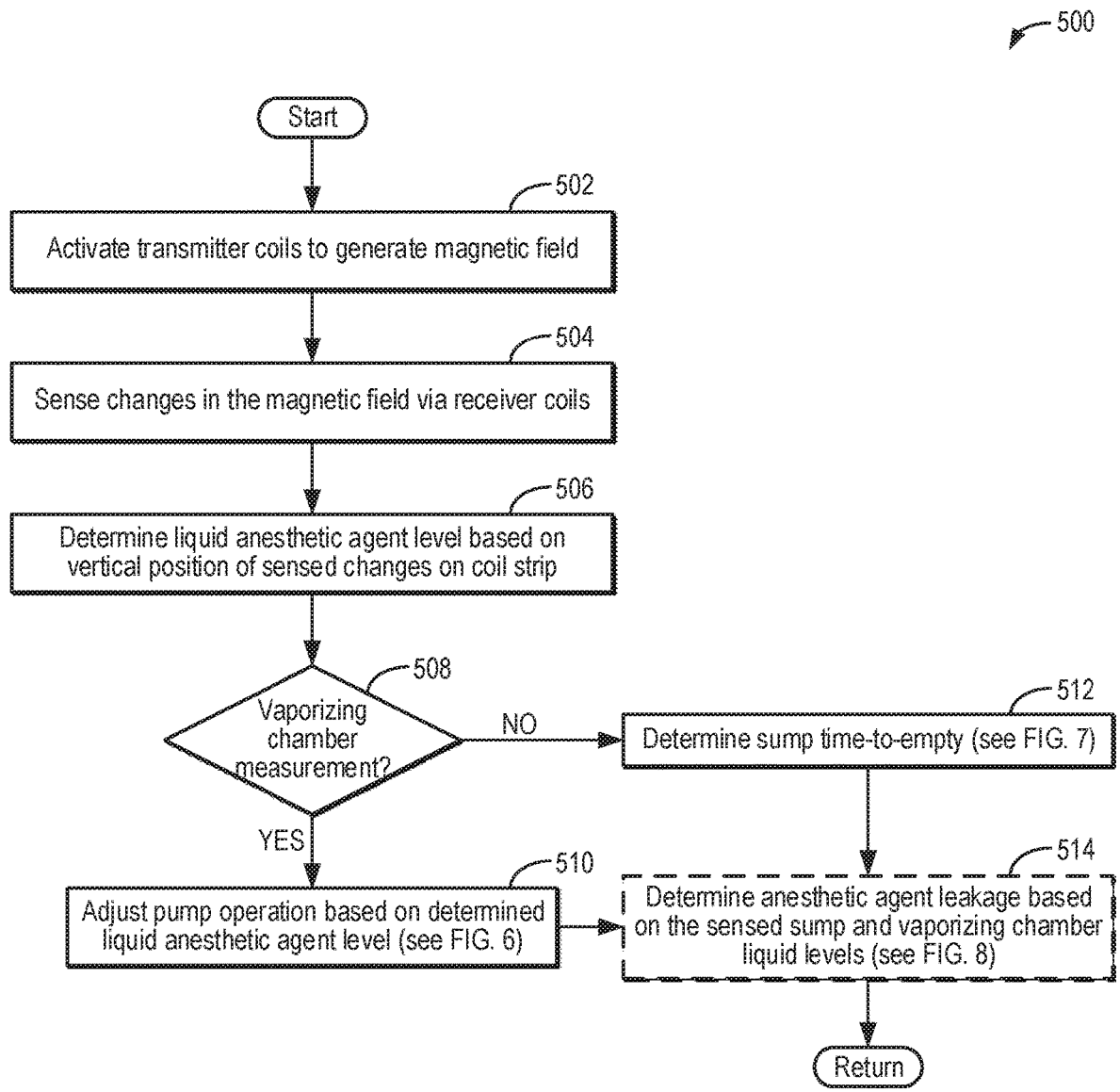
FIG. 5 is a high-level flow chart illustrating an exemplary embodiment of a method for measuring a liquid anesthetic agent level via an inductive level sensor.

Turning now to FIG. 5, a high-level flow chart of an example method 500 for determining a level (or volume) of liquid anesthetic agent in a chamber of an anesthetic vaporizer using an inductive level sensor and adjusting operation the anesthetic vaporizer based on the level is shown. The chamber may be a vaporizing chamber (e.g., vaporizing chamber 202 shown in FIGS. 2-4) or a sump (e.g., sump 222 of FIGS. 2-3), for example, based on a position of the inductive level sensor. Method 500 and the rest of the methods included herein may be executed by a controller, such as controller 225 of FIGS. 2 and 3, according to instructions stored in a memory of the controller and in conjunction with one or more inputs, such as inputs received from an operator via a human-machine interface (e.g., HMI 226 of FIGS. 2 and 3) and one or more sensors (e.g., inductive level sensor 224 of FIG. 2 or combined inductive level sensor 324 of FIG. 3). Further, the controller may output information to the operator of the anesthesia machine via the human-machine interface.

Transmitter coils are activated to generate a magnetic field at 502. For example, the controller may supply electrical power from a power source to flow current through the transmitter coils extending along a circuit board of the inductive level sensor. The current flow causes the transmitter coils to generate the magnetic field. While the circuit board is external to the chamber, the generated magnetic field penetrates the chamber to substantially surround a metallic-plated float (e.g., float 232 of FIGS. 2-4 or second float 332 of FIG. 3) that serves as a measurement target positioned within the chamber.

Changes in the magnetic field are sensed via receiver coils at 504. The metallic-plated float attenuates the magnetic field generated by the transmitter coil, which changes current flow through the receiver coils at the specific vertical location of the metallic-plated float. The receiver coils may output a signal, such as a voltage signal, to the controller that includes information regarding the vertical location of the attenuated magnetic field.

A liquid anesthetic agent level is determined based on a vertical position of the sensed changes in the magnetic field on the inductive coil strip at 506. Because the metallic-plated float sits on or at a surface of the liquid anesthetic agent in the chamber, the vertical location of the magnetic field attenuation also corresponds to the liquid level in the chamber. In some embodiments, the controller may determine the liquid anesthetic agent level by inputting the signal received from the receiver coils into a look-up table, function, or graph stored in memory, which may output the corresponding liquid level (or height). For example, the look-up table, function, or graph may take into account sensor calibrations, such as to account for a portion of the float above the liquid surface and a portion of the float below the liquid surface.

It is determined if the level measurement is a vaporizing chamber measurement at 508. In embodiments where a combined inductive level sensor is used or where two separate inductive level sensors are included in the anesthetic vaporizer, the controller may differentiate between anesthetic agent levels measured in the vaporizing chamber from anesthetic agent levels measured in the sump in order to execute an appropriate sub-routine using the level measurement. For example, the controller may determine that the level measurement is a vaporizing chamber measurement responsive to receiving the output from receiver coils that overlap with a float positioned in the vaporizing chamber. Conversely, the controller may determine that the level measurement is not a vaporizing chamber measurement responsive to receiving the output from receiver coils that overlap with a float positioned in the sump. In embodiments where only one inductive level sensor is included in the anesthetic vaporizer (and the combined inductive level sensor is not included), the controller may not differentiate between anesthetic agent levels measured in the vaporizing chamber from anesthetic agent levels measured in the sump but may automatically proceed to the appropriate sub-routine.

If the level measurement is a vaporizing chamber measurement, at 510, pump operation is adjusted based on the determined liquid anesthetic agent level, as will be elaborated below with respect to FIG. 6. In some embodiments, method 500 may optionally proceed to 514, and anesthetic agent leakage is determined based on the sensed (e.g., measured) sump and vaporizing chamber liquid levels, as will be elaborated below with respect to FIG. 8. Method 500 may then return so that another anesthetic agent level measurement may be performed, such as an updated level of anesthetic agent in the vaporizing chamber or a sump measurement. If the level measurement is not a vaporizing chamber measurement, such as when the level measurement is a sump measurement, at 512, a sump time-to-empty is determined, as will be described with respect to FIG. 7. Method 500 may return or may optionally proceed to 514 before returning, as described above.

Figure 6:
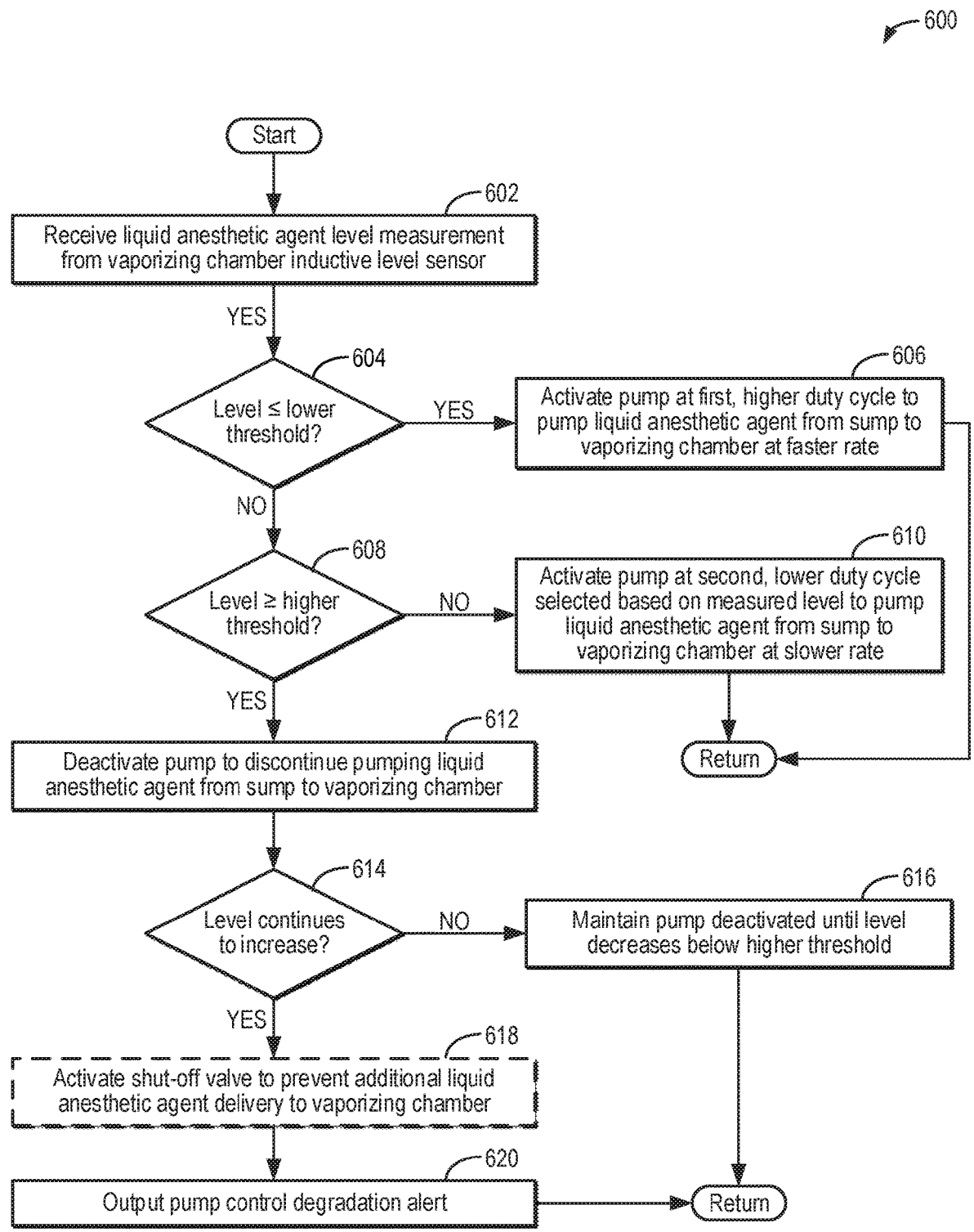
FIG. 6 is a flow chart illustrating an exemplary embodiment of a method for controlling operating of a pump based on a level of liquid anesthetic agent in a sump.

Continuing to FIG. 6, an example method 600 is provided for adjusting operation of a pump configured to deliver liquid anesthetic agent from a sump to a vaporizing chamber of an anesthetic vaporizer based on measurements received from a level sensor (e.g., inductive level sensor 224 of FIG. 2 or combined inductive level sensor 324 of FIG. 3). For example, method 600 of FIG. 6 may be performed by a controller (e.g., controller 225 of FIGS. 2 and 3) as a part of method 500 of FIG. 5 (e.g., at 510).

A liquid anesthetic agent level measurement is received from a vaporizing chamber inductive level sensor at 602. As described above, the controller may process an output signal from receiver coils of the inductive level sensor to relate the signal to the level.

At 604, it is determined if the liquid anesthetic agent level measurement is less than or equal to a (first) lower threshold. As described above with respect to FIG. 2, the lower threshold may be a pre-determined, non-zero level of the liquid anesthetic agent that is calibrated to maintain a minimum level of liquid anesthetic agent in the vaporizing chamber for desired vaporization properties.

Responsive to the liquid anesthetic agent level measurement being less than or equal to the lower threshold, method 600 proceeds to 606, and the pump is activated at a first, higher duty cycle to pump liquid anesthetic agent from the sump to the vaporizing chamber at a faster rate. For example, the controller may input the measured level of the liquid anesthetic agent into one or more look-up tables, functions, or graphs, which may output the first duty cycle. Method 600 may then return so that the pump operation may be adjusted as the liquid anesthetic agent level changes. As an example, as the measured level increases, the duty cycle of pump activation may decrease, and as the measured level decreases, the duty cycle of pump activation may increase.

Responsive to the measured liquid anesthetic agent level not being less than or equal to the lower threshold (e.g., the level measurement is greater than the lower threshold), method 600 proceeds to 608, and it is determined if the level is greater than or equal to a second, higher threshold. As also described above with respect to FIG. 2, the higher threshold may be a pre-determined, non-zero level of the liquid anesthetic agent that is calibrated to prevent overfilling of the vaporizing chamber and reduce vaporization variation.

Responsive to the measured liquid anesthetic agent level not being greater than or equal to the higher threshold (e.g., the level measurement is less than the higher threshold), method 600 proceeds to 610, and the pump is activated at a second, lower duty cycle to pump liquid anesthetic agent from the sump to the vaporizing chamber at a slower rate. For example, with the level greater than the lower threshold (e.g., minimum level) but less than the higher threshold (e.g., maximum level), the controller may continue to pump liquid anesthetic agent into the vaporizing chamber from the sump, which may decrease an amount of variation in the level. For example, the controller may input the measured level of the liquid anesthetic agent into the one or more look-up tables, functions, or graphs, which may output the second duty cycle. Alternatively, the controller may continue to operate the pump at the first duty cycle until the level reaches the higher threshold. Method 600 may then return so that the pump operation may be adjusted as the liquid anesthetic agent level changes, as described above.

Returning to 608, if instead the level is greater than or equal to the higher threshold, method 600 proceeds to 612, and the pump is deactivated to discontinue pumping the liquid anesthetic agent from the sump to the vaporizing chamber. In one example, the pump may remain powered "on," but activated at 0% duty cycle. In another example, the pump may be switched to an "off" or stand-by mode until the liquid anesthetic agent level decreases below the higher threshold.

It is determined if the liquid anesthetic agent level measurement continues to increase at 614. For example, even though the controller has commanded pumping to be discontinued, the liquid anesthetic agent level in the vaporizing chamber may continue to increase when pump control has become degraded, such as during a "runaway" condition. In contrast, during nominal conditions, the controller may expect the level of liquid anesthetic agent in the vaporizing chamber to decrease as anesthetic agent is supplied to a patient.

If the level does not continue to increase, method 600 proceeds to 616, and the pump is maintained deactivated until the level decreases below the higher threshold. In an alternative embodiment, the pump may be maintained deactivated until the level decreases to the lower threshold, decreasing an amount of time that the pump is activated. Method 600 may then return.

Returning to 614, if the measured liquid anesthetic agent level continues to increase, method 600 optionally proceeds to 618, and a shut-off valve is activated to prevent additional delivery liquid anesthetic agent delivery to the vaporizing chamber. As an example, 618 may be executed in anesthetic vaporizer embodiments that include a shut-off valve coupled between the sump and the vaporizing chamber (e.g., shut-off valve 218 of FIGS. 2 and 3). By activating the shut-off valve, the shut-off valve is actuated to a fully closed position, blocking flow from the pump to the vaporizing chamber even if the pump continues to operate. Instead, the liquid anesthetic agent may be recycled to the sump via a liquid return line (e.g., liquid return line 215). However, in embodiments that do not include the shut-off valve, 618 may be omitted. Whether or not the shut-off valve is included, the inductive level sensor may additionally include a self-sealing float (e.g., sealing disc 234 positioned on float 232 of FIGS. 2-4) that prevents liquid anesthetic agent from reaching a gas output manifold.

A pump control degradation alert is output at 620. The controller may output one or more alerts, such as one or more audio or visual alerts, via a human-machine interface (e.g., HMI 226 of FIGS. 2 and 3) to alert an operator of the anesthetic vaporizer to take an appropriate action. For example, even though the self-sealing float may prevent liquid accumulation in the gas output manifold, it may also prevent vaporized anesthetic agent from reaching the gas output manifold. Thus, in some examples, the anesthetic vaporizer may be unable to reliably deliver anesthetic agent to a patient while the pump control degradation exists. Method 600 may then return.

Figure 7:
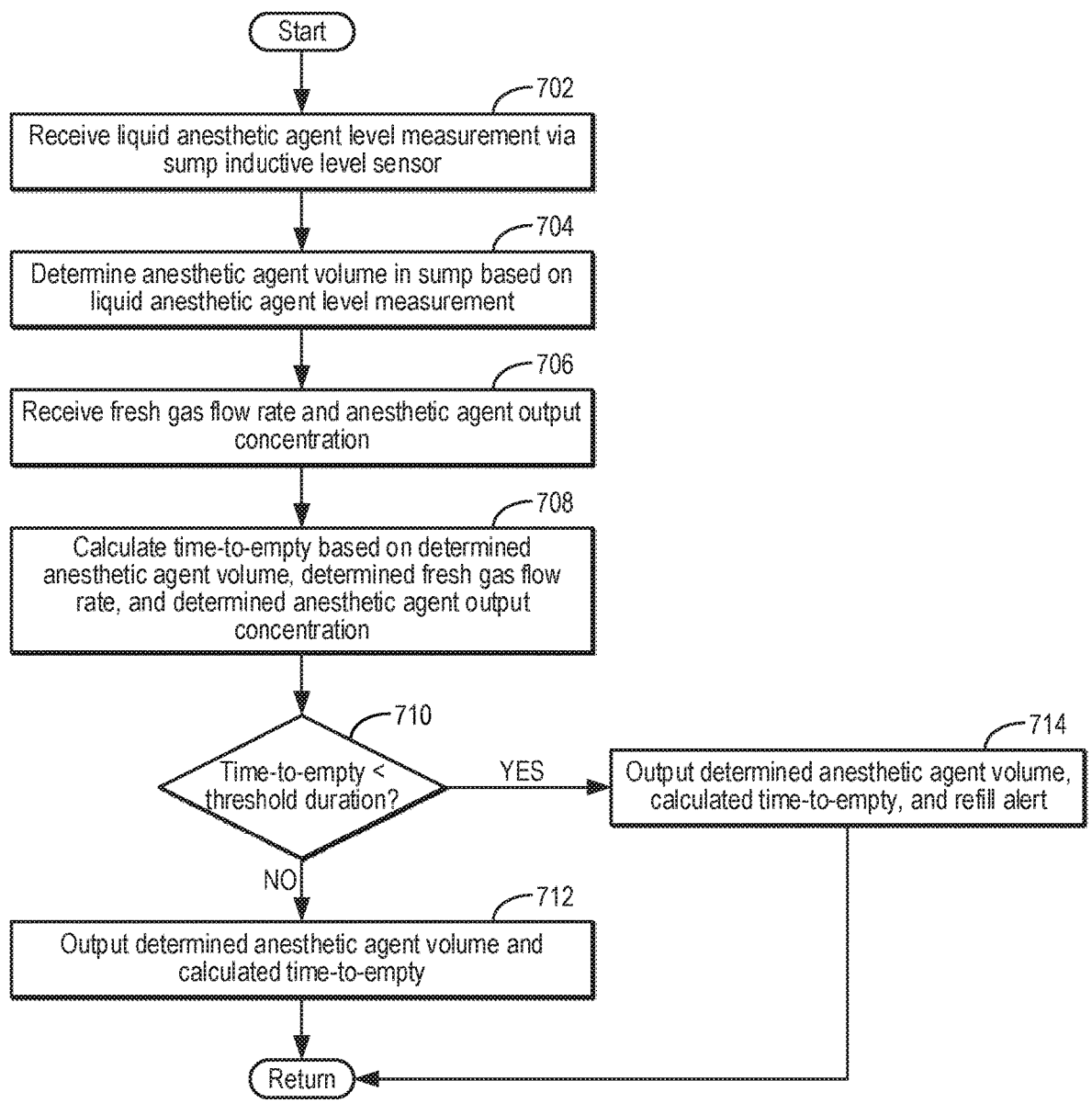
FIG. 7 is a flow chart illustrating an exemplary embodiment of a method for determining a time-to-empty of an anesthetic vaporizer sump based on measurements made by an inductive level sensor.

Next, FIG. 7 shows an example method 700 for determining a time-to-empty of a sump configured to supply liquid anesthetic agent to a vaporizing chamber of an anesthetic vaporizer based on measurements received from a level sensor (e.g., combined inductive level sensor 324 of FIG. 3). For example, method 700 of FIG. 7 may be performed by a controller (e.g., controller 225 of FIGS. 2 and 3) as a part of method 500 of FIG. 5 (e.g., at 512).

A liquid anesthetic agent level measurement is received from a sump inductive level sensor at 702. As described above, the controller may process an output signal from receiver coils of the inductive level sensor to relate the signal to the level. In embodiments including a combined inductive level sensor (e.g., the system of FIG. 3), the controller may receive the signal from an inductive coil strip positioned adjacent to and aligned with a measurement target within the sump (e.g., second inductive coil strip 337b), and not from an inductive coil strip positioned adjacent to and aligned with a measurement target within the vaporizing chamber (e.g., first inductive coil strip 337a).

The anesthetic agent volume in the sump is determined based on the liquid anesthetic agent level measurement at 704. The controller may store a pre-calibrated relationship between the measured level and the anesthetic agent volume in memory, such as stored as a graph, look-up table, or equation. Therefore, the controller may input the measured liquid anesthetic agent level into the graph, look-up table, or equation, which may output the corresponding anesthetic agent volume that produces the measured level. The pre-calibrated relationship may be specific to each sump configuration (e.g., volume capacity and/or geometry), as a same height of liquid anesthetic agent may have different volumes in different geometry sumps.

A fresh gas flow rate and an output anesthetic agent concentration are received at 706. For example, the controller may receive a measurement of a concentration of anesthetic agent output by the anesthetic vaporizer to a patient from a concentration sensor (e.g., concentration sensor 256 of FIG. 2) and a fresh gas flow rate measurement indicative of the flow rate of the fresh gas into the anesthetic vaporizer from a mass flow sensor (e.g., first mass flow sensor 241). Alternatively, the controller may receive an output anesthetic agent concentration setpoint and a fresh gas flow rate setpoint from an operator via a human-machine interface (e.g., HMI 226 of FIGS. 2 and 3). For example, the controller may use the setpoints when measured values are unavailable.

A time-to-empty is calculated based on the determined anesthetic agent volume (e.g., as determined at 704), the fresh gas flow rate, and the output anesthetic agent concentration at 708. The time-to-empty refers to a remaining time duration until the volume liquid anesthetic agent in the sump is depleted. Additionally or alternatively, the time-to-empty refers to a remaining operational time of the anesthetic vaporizer using the current operating conditions. In one embodiment, the time-to-empty may correspond to the remaining time duration until the volume of liquid anesthetic reaches zero (e.g., the sump is completely empty). In another embodiment, the time-to-empty may correspond to the remaining time duration until the volume of liquid anesthetic reaches a non-zero volume, such as a lowest measureable volume by the level sensor.

In one embodiment, the controller may calculate the time-to-empty based on a running average the fresh gas flow rate (e.g., over a predetermined duration of anesthetic agent usage, such as a duration in a range from 1 to 5 minutes), a running average of the output anesthetic agent concentration (e.g., over the duration), and the determined anesthetic agent volume in the sump into one or more look-up tables, graphs, or equations. As one example, the controller may calculate the time-to-empty using the following equations:

$$\text{Saturated\_Gas\_Volume} = \frac{SW \cdot GC \cdot (273 + T)}{MW \cdot 273} \quad \text{(Equation 1)}$$

$$\text{Time\_to\_Empty} = \frac{\text{Volume\_in\_Sump} \times \text{Saturated\_Gas\_Volume} \times 100}{\text{Ave\_FGF} \times \text{Ave\_Agent\_Conc}} \quad \text{(Equation 2)}$$

Equation 1 results in the term Saturated_Gas_Volume (in milliliters, mL), which corresponds to an amount of vaporized anesthetic agent produced at a given temperature (T) of the anesthetic agent for the type of anesthetic agent being used. The term SW is the specific weight of the anesthetic agent in g/mL, which is selected based on the type of anesthetic agent being used (e.g., 1.49 g/mL for isoflurane, 1.53 g/mL for sevoflurane, or 1.47 g/mL for desflurane). For example, the controller may input the type of anesthetic agent into a look-up table, which may output the specific weight of the given type of anesthetic agent. The term GC is Avogadro's gas constant, which is a universal constant for all gases (e.g., independent of the type of anesthetic agent being used) that defines that at standard conditions for temperature and pressure, dry (e.g., STPD, corresponding to a temperature of 273 K and a pressure of 1 atmosphere, without water vapor), one mole of any gas contains 6.022×$10^{23}$ molecules, which occupy a volume of 22,400 mL. The term MW is the molecular weight of the anesthetic agent being used in g/mol, which is selected based on the type of anesthetic agent being used (e.g., 184 g/mol for isoflurane, 200 g/mol for sevoflurane, or 168 g/mol for desflurane). For example, the controller may input the type of anesthetic agent into a separate look-up table, which may output the molecular weight of the given type of anesthetic agent.

The Saturated_Gas_Volume calculated via Equation 1 may be used in Equation 2 to determine Time_to_Empty (in minutes), which corresponds to the duration of time remaining before the sump is emptied at the current anesthetic agent usage rate. In Equation 2, the term Ave_FGF is the average fresh gas flow rate (in mL/min), the term Ave_Agent_Conc is the average output anesthetic agent concentration (in % volume), and the term Volume_in_Sump is the anesthetic agent volume determined via the level measurement from the sump inductive level sensor (e.g., at 704).

It is determined if the time-to-empty is less than a threshold duration at 710. The threshold duration may be a non-zero time duration corresponding to a remaining time of anesthetic agent usage below which refilling the sump is indicated. For example, the threshold duration may provide a time buffer to account for an anticipated amount of time it may take the operator to refill the sump, thereby reducing instances of the sump becoming completely empty (or reaching a non-zero minimum volume).

If the time-to-empty is not less than the threshold duration, method 700 proceeds to 712, and the determined anesthetic agent volume and the calculated time-to-empty are output. For example, the controller may output the determined anesthetic agent volume (e.g., determined at 704) and the calculated time-to-empty (e.g., calculated at 708) via the human-machine interface, such as via one or more of a visual and an audible message. Method 700 may then return so that the anesthetic agent volume and the time-to-empty may be updated as new measurements are received from the sump inductive level sensor.

If the time-to-empty is less than the threshold duration, method 700 proceeds to 714, and the determined anesthetic agent volume, the calculated time-to-empty, and a refill alert are output. For example, in addition to outputting the determined anesthetic agent volume and the calculated time-to-empty, as described above at 712, the controller may communicate the refill alert via the human-machine interface. In one embodiment, the refill alert may include an audible alarm or message. In another embodiment, the refill alert may additionally or alternatively include a visual message. Method 700 may then return.

Figure 8:
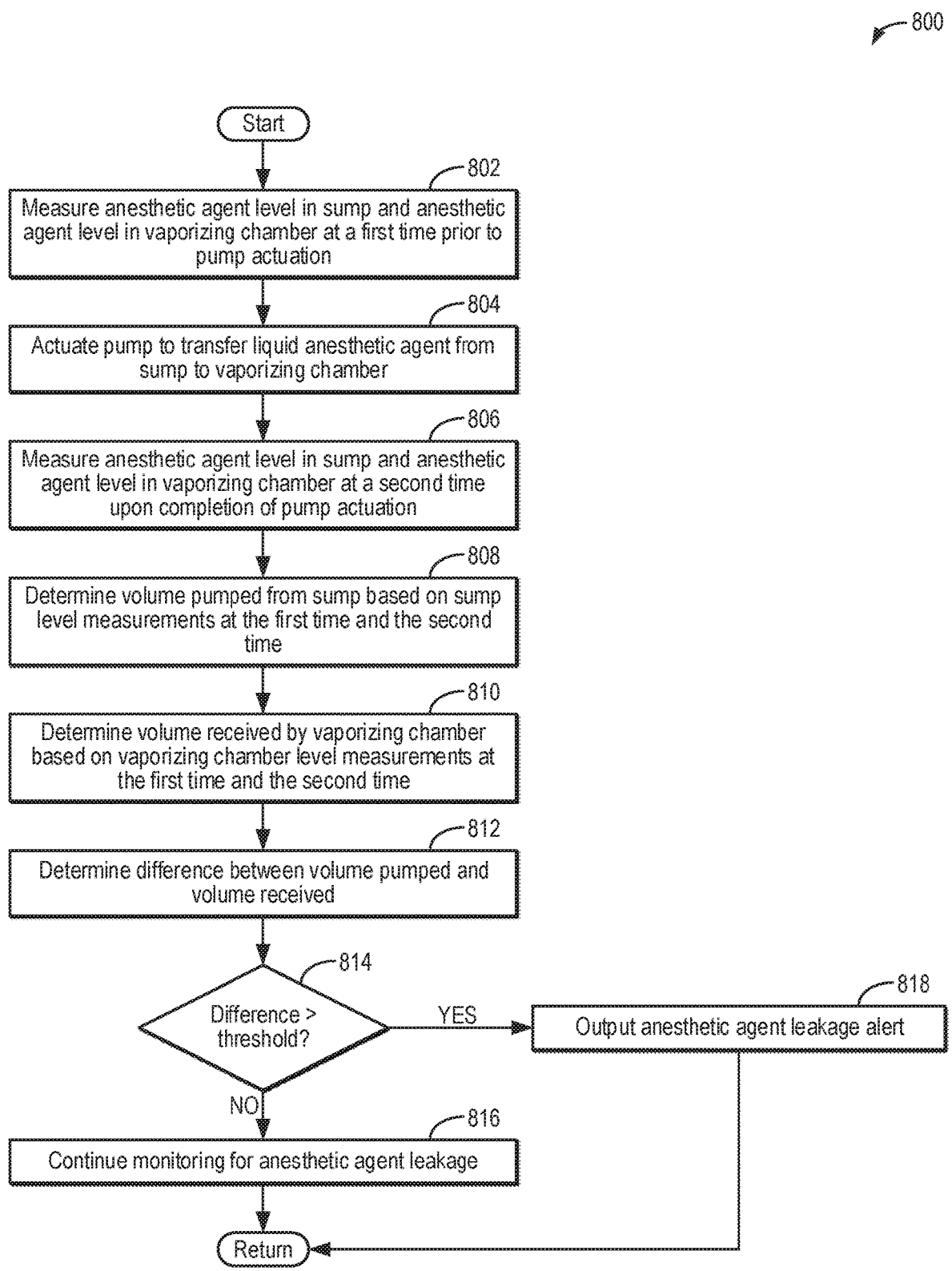
FIG. 8 is a flow chart illustrating an exemplary embodiment of a method for determining anesthetic agent leakage based on measurements made by an inductive level sensor.

Next, FIG. 8 shows an example method 800 for anesthetic agent leak detection based on measurements received from an inductive level sensor (e.g., combined inductive level sensor 324 of FIG. 3). For example, method 800 of FIG. 8 may be performed by a controller (e.g., controller 225 of FIGS. 2 and 3) as a part of method 500 of FIG. 5 (e.g., at 514). Leakage may occur at one or more seal locations of an anesthetic vaporizer, such as at a fill assembly of a sump, at a pump coupled between the sump and a vaporizing chamber, etc., due to degradation of the seal, and timely detection of the leak may reduce environmental exposure to the anesthetic agent as well as anesthetic agent waste.

At 802, an anesthetic agent level in the sump and an anesthetic agent level in the vaporizing chamber are measured at a first time that is prior to pump actuation. As described above with respect to FIG. 5, performing the level measurement may include activating transmitter coils to generate a magnetic field and detecting magnetic field attenuation caused by a metallic-plated float via receiver coils. For example, the anesthetic agent level in the vaporizing chamber at the first time (e.g., a first vaporizing chamber level measurement) may correspond to a signal received from a first set of receiver coils positioned to detect a vertical position of a first float positioned within the vaporizing chamber, and the anesthetic agent level in the sump at the first time (e.g., a first sump level measurement)

may correspond to a signal received from a second set of receiver coils positioned to detect a vertical position of a second float positioned within the sump.

At 804, the pump is actuated to transfer liquid anesthetic agent from the sump to the vaporizing chamber. As one example, the pump may be actuated to perform a single pump stroke. In other examples, the pump may be actuated for a duration at a specified duty cycle, such as elaborated above at FIG. 6.

At 806, the anesthetic agent level in the sump and the anesthetic agent level in the vaporizing chamber are measured at a second time upon completion of the pump actuation. For example, responsive to deactivation of the pump, the controller may obtain a second sump level measurement and a second vaporizing chamber measurement via the combined inductive level sensor.

At 808, a volume pumped from the sump is determined based on the sump level measurements at the first time and the second time. For example, the controller may input a difference between the first sump level measurement and the second sump level measurement into a look-up table, function, or graph, which may output the corresponding volume pumped.

At 810, a volume received by the vaporizing chamber is determined based on the vaporizing chamber measurements at the first time and the second time. For example, the controller may input a difference between the first vaporizing chamber level measurement and the second vaporizing chamber level measurement into a look-up table, function, or graph, which may output the corresponding volume received.

At 812, a difference between the volume pumped and the volume received is determined. As one example, the controller may subtract the volume pumped from the volume received to determine the difference. As another example, the controller may determine a percentage difference between the volume pumped and the volume received.

At 814, it is determined if the difference between the volume pumped and the volume received is greater than a threshold. The threshold may be a non-zero, pre-calibrated difference or percentage difference between the volume pumped and the volume received that may distinguish minor variances due to consumption of anesthetic agent in the vaporizing chamber during the measurements from differences due to leakage, for example.

When the difference is not greater than the threshold, the volume pumped may be considered to be substantially equal to the volume received, and method 800 proceeds to 816 to continue monitoring for anesthetic agent leakage. Method 800 may then return. For example, the controller may perform new sump and vaporizing chamber anesthetic agent level measurements prior to a subsequent pump actuation in order to continuously monitor for anesthetic agent leakage.

When the difference is greater than the threshold, it may be determined that anesthetic agent leakage is occurring, and method 800 proceeds to 818 to output a leakage alert. For example, the controller may output the alert via a human-machine interface (e.g., HMI 226 shown in FIGS. 2 and 3). As one example, the alert may include an audible alarm or message. As another example, the alert may additionally or alternatively include a visual message. The message may indicate that anesthetic agent leakage is occurring and that anesthetic vaporizer service is recommended, for example. The message may be communicated to an operator of the anesthetic vaporizer, for example. In this way, the level measurements obtained via one or more inductive level sensors may be used to determine and indicate that an anesthetic agent leak is occurring.

Thus, the systems and methods described herein provide for determining and tracking a level and/or volume of an anesthetic agent in a liquid-holding chamber of an anesthetic vaporizer via a non-contact inductive level sensor. Further, by determining the volume via an inductive level sensor, the measurement will not be impacted by characteristics of the anesthetic agent, which may change over time (due to a reactivity of the anesthetic agent, a temperature of the anesthetic agent, humidity, etc.). Further, the inductive level sensor is may be adapted to measure the level of liquid anesthetic agent in a vaporizing chamber and/or a sump. In particular, a heat pipe extending into the vaporizing chamber may serve as a support rod for a float measurement target positioned within the vaporizing chamber, while the float may include a sealing disc to self-seal the vaporizing chamber during an overfilling condition. By including a combined inductive level sensor for measuring both the vaporizing chamber and the sump, sensor costs may be reduced while the sensor may output two separate signals. The separate signals may be used by an electronic controller differently, such as to adjust pump operation based on the vaporizing chamber signal and output a refill alert based on the sump signal. A technical effect of including a sealing disc on a top surface of a float of an inductive level sensor is that a gas output manifold may be sealed during an overfilling condition while simultaneously measuring a level of liquid anesthetic agent in a vaporizing chamber.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for an inductive level sensor for an anesthetic vaporizer, comprising:
   a measurement target positioned around a rod that extends within a chamber configured to hold liquid anesthetic agent, the rod configured to be at least partially submerged in the liquid anesthetic agent and the measurement target configured to slide vertically along a length of the rod and rest on a surface of the liquid anesthetic agent; and a strip of inductive transmitter coils and receiver coils positioned external to the chamber, a length of the strip aligned with the length of the rod, the transmitter coils configured to generate a magnetic field that surrounds the rod and the measurement target and the receiver coils configured to sense changes in the generated magnetic field at a vertical location of the measurement target on the rod.

2. The system of claim 1, wherein the chamber is a vaporizing chamber configured to receive the liquid anesthetic agent from a sump via a pump, and the measurement target includes a sealing disc coupled to a top surface of a metallic-plated float.

3. The system of claim 2, wherein the vaporizing chamber is defined by a housing and includes a gas passage opening in a top of the housing, and wherein the sealing disc forms a liquid-tight seal with the gas passage opening when the sealing disc presses against an interior surface of the top of the housing.

4. The system of claim 2, wherein the anesthetic vaporizer includes a heat pipe, a first portion of the heat pipe external to the vaporizing chamber a second portion of the heat pipe crossing the barrier and extending into the vaporizing chamber, and wherein the second portion of the heat pipe comprises the rod.

5. The system of claim 4, wherein the anesthetic vaporizer further includes an inductive heating element positioned exterior to the vaporizing chamber, the inductive heating element operated to selectively heat a ferromagnetic collar in contact with the first portion of the heat pipe.

6. The system of claim 2, further comprising a controller storing executable instructions in non-transitory memory that, when executed, cause the controller to:
actuate the transmitter coils to generate the magnetic field;
determine the vertical location of the measurement target on the rod based on the changes in the generated magnetic field sensed by the receiver coils;
determine a level of the liquid anesthetic agent in the vaporizing chamber based on the determined vertical location; and
adjust a duty cycle of the pump based on the determined level of the liquid anesthetic agent.

7. The system of claim 1, wherein the chamber is a sump configured to supply the liquid anesthetic to a vaporizing chamber via a pump, and the system further comprises a controller storing executable instructions in non-transitory memory that, when executed, cause the controller to:
actuate the transmitter coils to generate the magnetic field;
determine the vertical location of the measurement target on the rod based on the changes in the generated magnetic field sensed by the receiver coils;
determine a volume of the liquid anesthetic agent in the sump based on the determined vertical location;
calculate a remaining time until the sump is empty based on the determined volume; and
output a refill alert responsive to the remaining time decreasing below a threshold.

8. The system of claim 1, wherein the measurement target includes a core comprised of one or more of polypropylene, nylon, and ultrahigh molecular weight polyethylene.

9. The system of claim 8, wherein the measurement target further includes metal plating on a surface of the core, the metal plating comprised of one or more of nickel, brass, and stainless steel.

10. A method for measuring a level of liquid anesthetic agent in an anesthetic vaporizer, comprising:
activating transmitter coils of an inductive level sensor to generate magnetic field, the transmitter coils included in a vertical coil strip external to a chamber holding liquid anesthetic agent and aligned with a measurement target that floats on a surface of the liquid anesthetic agent within the chamber;
sensing changes in the magnetic field produced by the measurement target via receiver coils of the inductive level sensor;
determining the level of the liquid anesthetic agent based on a vertical position of the changes in the magnetic field; and
adjusting operation of the anesthetic vaporizer based on the determined level of the liquid anesthetic agent.

11. The method of claim 10, wherein the chamber holding the liquid anesthetic agent is a vaporizing chamber, and adjusting operation of the anesthetic vaporizer based on the determined level of the liquid anesthetic agent includes adjusting a duty cycle of a pump based on the determined level of the liquid anesthetic agent, the pump positioned to deliver the liquid anesthetic agent to the vaporizing chamber.

12. The method of claim 11, wherein adjusting the duty cycle of the pump based on the determined level of the liquid anesthetic agent includes:
activating the pump at a first, higher duty cycle responsive to the determined level being less than or equal to a lower threshold;
activating the pump at a second, lower duty cycle responsive to the determined level being less than a higher threshold; and
deactivating the pump responsive to the determined level being greater than or equal to the higher threshold.

13. The method of claim 10, further comprising heating the liquid anesthetic agent within the chamber via a heat pipe including a rod that extends into the liquid anesthetic agent, and wherein the measurement target comprises a ring positioned around the rod.

14. The method of claim 10, wherein the chamber holding the liquid anesthetic agent is a sump, and adjusting operation of the anesthetic vaporizer based on the determined level of the liquid anesthetic agent includes:
calculating a time-to-empty based on the determined level of the liquid anesthetic agent; and
outputting the time-to-empty via an audible or visual message.

15. The method of claim 14, further comprising outputting a refill alert via an audible or visual alarm responsive to the time-to-empty being less than a threshold duration.

16. A system for an anesthetic vaporizer, comprising:
a sump configured to hold a liquid anesthetic agent;
a vaporizing chamber configured to receive the liquid anesthetic agent from the sump via a pump;
a first inductive level sensor, the first inductive level sensor including a first float positioned on a first rod configured to be at least partially submerged in the liquid anesthetic agent within the vaporizing chamber, a sealing disc positioned on a top surface of the first float, the first inductive level sensor further including a first strip of inductive coils external to the vaporizing chamber, the first strip of inductive coils aligned with a length of the first rod; and
a controller storing executable instructions in non-transitory memory that, when executed, cause the controller to:

generate a first magnetic field that surrounds the first rod and the first float via a first coil type of the first strip of inductive coils;

sense changes in the first magnetic field produced by the first float via a second coil type of the first strip of inductive coils;

determine a level of the liquid anesthetic agent in the vaporizing chamber based on a vertical location of the sensed changes; and adjust a duty cycle of activation of the pump based on the determined level of the liquid anesthetic agent in the vaporizing chamber.

17. The system of claim 16, further comprising a second inductive level sensor, the second inductive level sensor including a second float positioned on a second rod configured to be at least partially submerged in the liquid anesthetic agent within the sump, the second inductive level sensor further including a second strip of inductive coils external to the sump, the second strip of inductive coils aligned with a length of the second rod and not the first rod; and wherein the controller includes further instructions stored in non-transitory memory that, when executed, cause the controller to:

generate a second magnetic field that surrounds the second rod and the second float via a first coil type of the second strip of inductive coils;

sense changes in the magnetic field produced by the second float via a second coil type of the second strip of inductive coils;

determine a level of the liquid anesthetic agent in the sump based on a vertical location of the sensed changes; and output a time-to-empty to a display based on the determined level of the liquid anesthetic agent in the sump.

18. The system of claim 17, wherein the first strip of inductive coils and the second strip of inductive coils are etched on a same circuit board positioned intermediate the vaporizing chamber and the sump and having a length and height that extends parallel to a length and height of each of the chamber and sump.

19. The system of claim 16, further comprising a gas passage opening in a top housing of the vaporizing chamber, and wherein the sealing disc is configured to cover the gas passage opening when pressed into the top housing.

20. The system of claim 16, wherein the first rod is a portion of a heat pipe that vertically extends into the vaporizing chamber.

* * * * *